(12) United States Patent
Kobayashi et al.

(10) Patent No.: US 9,895,210 B2
(45) Date of Patent: Feb. 20, 2018

(54) ELECTRIC LINEAR ACTUATOR AND OUTPUT SHAFT VIBRATION-TYPE ELECTRIC DEVICE WITH SAID ELECTRIC LINEAR ACTUATOR

(71) Applicant: Panasonic Intellectual Property Management Co., Ltd., Osaka (JP)

(72) Inventors: Noboru Kobayashi, Osaka (JP); Masashi Moriguchi, Shiga (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 307 days.

(21) Appl. No.: 14/653,700

(22) PCT Filed: Dec. 12, 2013

(86) PCT No.: PCT/JP2013/007326
§ 371 (c)(1),
(2) Date: Jun. 18, 2015

(87) PCT Pub. No.: WO2014/103226
PCT Pub. Date: Jul. 3, 2014

(65) Prior Publication Data
US 2016/0000543 A1 Jan. 7, 2016

(30) Foreign Application Priority Data
Dec. 27, 2012 (JP) .................. 2012-286269

(51) Int. Cl.
*H02K 33/00* (2006.01)
*A61C 17/34* (2006.01)
*H02K 33/06* (2006.01)

(52) U.S. Cl.
CPC .......... *A61C 17/34* (2013.01); *A61C 17/3445* (2013.01); *A61C 17/3481* (2013.01); *H02K 33/00* (2013.01); *H02K 33/06* (2013.01)

(58) Field of Classification Search
CPC .......... H02K 66/00; H02K 7/145; H02K 7/14; H02K 7/16; H02K 33/06; H02K 33/00
(Continued)

(56) References Cited

U.S. PATENT DOCUMENTS 3,484,629 A * 12/1969 Kunz .................. H02K 33/06
310/15
4,831,292 A * 5/1989 Berry .................. H02K 33/06
310/15
(Continued)

FOREIGN PATENT DOCUMENTS

JP 09-252843 A 9/1997
JP 2002-176758 A 6/2002
(Continued)

OTHER PUBLICATIONS

Machine translation of JP4487650, cited in Applicant Admitted Prior Art.*
(Continued)

*Primary Examiner* — Forrest M Phillips
(74) *Attorney, Agent, or Firm* — McDermott Will & Emery LLP

(57) ABSTRACT

An electric linear actuator includes a fixed block, an output movable block, a counter movable block, a projecting side coupling member, a retracting side coupling member, a block coupling member, and an output functional member. The output movable block and the counter movable block are configured to be reciprocated in the movable direction in opposite phases by electromagnetic force acting between the fixed block and the output and counter movable blocks. The projecting side coupling member is coupled to the output movable block and the counter movable block. The retracting side coupling member is coupled to the output movable block and the counter movable block. The projecting side
(Continued)

coupling member and the retracting side coupling member have different shapes.

14 Claims, 17 Drawing Sheets

(58) Field of Classification Search
USPC .......................................................... 310/50
See application file for complete search history.

(56) References Cited

U.S. PATENT DOCUMENTS

| 7,122,921 | B2* | 10/2006 | Hall ..................... | A61C 17/16 |
| | | | | 15/22.1 |
| 7,876,003 | B2* | 1/2011 | Bax ..................... | A61C 17/22 |
| | | | | 15/21.1 |
| 8,661,596 | B2* | 3/2014 | Jungnickel ......... | A61C 17/3418 |
| | | | | 15/22.1 |
| 2005/0134123 | A1 | 6/2005 | Kobayashi et al. | |
| 2006/0158048 | A1* | 7/2006 | Kobayashi ......... | A61C 17/3445 |
| | | | | 310/12.04 |
| 2012/0074796 | A1* | 3/2012 | Kobayashi ........... | H02K 33/16 |
| | | | | 310/25 |

FOREIGN PATENT DOCUMENTS

| JP | 3475949 B2 | 12/2003 |
| JP | 2005-185067 A | 7/2005 |
| JP | 2009-240046 A | 10/2009 |
| JP | 4487650 B2 | 6/2010 |

OTHER PUBLICATIONS

International Search Report issued in PCT/JP2013/007326, dated Mar. 4, 2014, with English translation.
English Translation of International Preliminary Report on Patentability issued in International Application No. PCT/JP2013/007326 dated Jun. 30, 2015.

* cited by examiner

ELECTRIC LINEAR ACTUATOR AND OUTPUT SHAFT VIBRATION-TYPE ELECTRIC DEVICE WITH SAID ELECTRIC LINEAR ACTUATOR

RELATED APPLICATIONS

This application is the U.S. National Phase under 35 U.S.C. § 371 of International Application No. PCT/JP2013/007326, filed on Dec. 12, 2013, which in turn claims the benefit of Japanese Application No. 2012-286269, filed on Dec. 27, 2012, the disclosures of which Applications are incorporated by reference herein.

TECHNICAL FIELD

The present invention relates to an electric linear actuator and an output shaft vibration-type electric device including the electric linear actuator.

BACKGROUND ART

Conventional electric linear actuators can be classified into, for example, three types in accordance with the driving system. In the description given below, the three types of conventional electric linear actuators are referred to as a first conventional actuator 910, a second conventional actuator 920, and a third conventional actuator 930.

FIG. 22 illustrates an example of the first conventional actuator 910. The first conventional actuator 910 includes a casing 911, a fixed element 912, a movable element 916, and a movable element spring 917.

The casing 911 accommodates an output shaft 918 of an electric device, the fixed element 912, the movable element 916, and the movable element spring 917. The fixed element 912 is fixed to the casing 911. The fixed element 912 includes a coil 913, two permanent magnets 914, and four yokes 915. The coil 913, the permanent magnets 914, and the yokes 915 each have an annular shape. The movable element 916 is fixed to the output shaft 918. The movable element spring 917 is arranged between the casing 911 and the movable element 916. The movable element spring 917 applies force, acting in an axial direction of the output shaft 918, to the movable element 916.

The first conventional actuator 910 switches the direction of current supplied to the coil 913 to reciprocate the movable element 916 and the output shaft 918. However, in the first conventional actuator 910, unwanted vibration occurs due to the inertial force of the movable element 916. Patent Document 1 discloses an example of the first conventional actuator 910.

The second conventional actuator 920 includes a technique of reducing the unwanted vibration of the movable element 916. FIG. 23 illustrates an example of the second conventional actuator 920. The second conventional actuator 920 has a structure substantially the same as that of the first conventional actuator 910 except in that a weight 921, an intermediate spring 922, and a weight spring 923 are provided.

The weight 921 is arranged around a portion of the output shaft 918. The weight 921 moves relative to the output shaft 918 in the axial direction. The intermediate spring 922 is arranged between the movable element 916 and the weight 921. The intermediate spring 922 applies force, acting in the axial direction of the output shaft 918, to the movable element 916 and the weight 921. The weight spring 923 is arranged between the casing 911 and the weight 921. The weight spring 923 applies force, acting in the axial direction of the output shaft 918, to the weight 921.

The second conventional actuator 920 supplies the coil 913 with current, having a frequency close to the natural frequency in a secondary vibration mode. By supplying the current to the coil 913, the second conventional actuator 920 reciprocates the movable element 916 and the weight 921 in opposite phases. Thus, the unwanted vibration of the movable element 916 is reduced. However, the second conventional actuator 920 includes the weight 921 and thus has a larger size than the first conventional actuator 910. Patent Document 2 discloses an example of the second conventional actuator 920.

The third conventional actuator 930 includes a technique with which a smaller size and a higher efficiency can be achieved. FIG. 24 illustrates an example of the third conventional actuator 930. The third conventional actuator 930 includes an electromagnetic core block 931, two magnetic blocks 934, a block coupling member 937, a first coupling member 938, and a second coupling member 939.

The electromagnetic core block 931 is coupled to the block coupling member 937. The electromagnetic core block 931 includes a core 932 and a coil 933. Each magnetic block 934 is coupled to the block coupling member 937. Each magnetic block 934 reciprocates in the sideward direction as viewed in FIG. 24. The two magnetic blocks 934 are arranged in parallel in a direction (vertical direction as viewed in the drawing) orthogonal to the direction in which the magnetic blocks 934 reciprocate. FIG. 24 illustrates one of the two magnetic blocks 934. The other one of the magnetic blocks 934 (not shown) is arranged at a farther side of the illustrated magnetic block 934 in the vertical direction as viewed in the drawing. Each magnetic block 934 includes a permanent magnet 935 and a back yoke 936. The permanent magnet 935 and the electromagnetic core block 931 are opposed to each other with a gap in between.

The first coupling member 938 is arranged on one end side of each magnetic block 934 in the reciprocation direction of the magnetic block 934. The one magnetic block 934 and the other magnetic block 934 are coupled to each other by the first coupling member 938. The second coupling member 939 is arranged on the other end side of each magnetic block 934 in the reciprocation direction of the magnetic block 934. The second coupling member 939 couples the two magnetic blocks 934.

The third conventional actuator 930 supplies current to the coil 933 to reciprocate the two magnetic blocks 934 in opposite phases. This reduces unwanted vibration of the magnetic block 934. In the third conventional actuator 930, the two magnetic blocks 934 are arranged in parallel. Thus, the length in the reciprocation direction can be shortened compared with the second conventional actuator 920. Patent Document 3 illustrates an example of the third conventional actuator 930.

PATENT DOCUMENTS

Patent Document 1: Japanese Laid-Open Patent Publication No. 2002-176758
Patent Document 2: Japanese Patent No. 3475949
Patent Document 3: Japanese Patent No. 4487650

SUMMARY OF THE INVENTION

The electric linear actuator can be used in an output shaft vibration-type electric device. The output shaft vibration-type electric device reciprocates the output shaft with the electric linear actuator. Patent Documents 1 and 2 each disclose an electric toothbrush as an example of the output shaft vibration-type electric device.

The inventors of the present application have studied the use of an electric linear actuator having a structure similar to that of the third conventional actuator 930 in an output shaft vibration-type electric device. FIG. 25 illustrates an electric oral hygiene device 940 as an example of the output shaft vibration-type device.

The electric oral hygiene device 940 includes an electric linear actuator 941 as a driving source, an output shaft 943, a device functional member 944, and a main body casing 945. The main body casing 945 accommodates the electric linear actuator 941. The electric linear actuator 941 has a structure that is substantially the same as that of the third conventional actuator 930 except in that an output functional member 942 is provided.

The output functional member 942 is coupled to one of the magnetic blocks 934 by the block coupling member 937. The output functional member 942 is formed as a member for coupling the output shaft 943. The output shaft 943 is coupled to the output functional member 942. The device functional member 944 is coupled to the output shaft 943.

Each magnetic block 934 reciprocates in a projecting direction (left direction in FIG. 24) and a retracting direction (right direction in FIG. 24). The first coupling member 938 is arranged further in the projecting direction from each magnetic block 934. The first coupling member 938 couples the two magnetic blocks 934 to each other. The second coupling member 939 is arranged further in the retracting direction from each magnetic block 934. The second coupling member 939 couples the two magnetic blocks 934 to each other.

The inventors of the present application have found the following problems in the electric oral hygiene device 940.

The electric linear actuator 941 has the output functional member 942. Thus, the load applied to one of the magnetic blocks 934 differs between the ends of the magnetic block 934 at the protruding and retracting sides. Thus, the preferred spring constant differs between the first coupling member 938 and the second coupling member 939.

Different loads are not supposed to be applied to the two ends of the magnetic block in Patent Document 3. Thus, when the electric linear actuator in Patent Document 3 is used in the electric oral hygiene device, the spring constants of the first coupling member 938 and the second coupling member 939 may differ from the preferred spring constants. When the spring constants of the first coupling member 938 and the second coupling member 939 are inappropriately set, the driving efficiency of the electric actuator is low. The problem of the electric linear actuator described above assumes that the electric oral hygiene device is the output shaft vibration-type electric device. However, the same problem occurs in electric linear actuators of output shaft vibration-type electric devices other than the electric oral hygiene device.

Accordingly, it is an object of the present invention to provide an electric linear actuator having a high driving efficiency and an output shaft vibration-type electric device including the electric linear actuator.

One aspect of the present invention is an electric linear actuator that drives an output shaft of an output shaft vibration-type electric device. The electric linear actuator includes a fixed block, an output movable block, a counter movable block, a projecting side coupling member, a retracting side coupling member, a block coupling member, and an output functional member. The electric linear actuator is configured to reciprocate in a projecting direction and a retracting direction that define a movable direction. The output movable block and the counter movable block are arranged in parallel in a direction orthogonal to the movable direction. The block coupling member is coupled to the fixed block, the output movable block, and the counter movable block. The output movable block and the counter movable block are reciprocated in the movable direction in opposite phases by electromagnetic force acting between the fixed block and the output and counter movable blocks. The output functional member is movably coupled to the output movable block, and the output functional member includes a portion arranged further in the projecting direction than the block coupling member. The projecting side coupling member is arranged further in the projecting direction than the block coupling member and is coupled to the block coupling member. The retracting side coupling member is arranged further in the retracting direction than the block coupling member and is coupled to the block coupling member. The projecting side coupling member and the retracting side coupling member have different shapes.

A further aspect of the present invention is an electric linear actuator that drives an output shaft of an output shaft vibration-type electric device. The electric linear actuator includes an output movable block, a counter movable block, a projecting side coupling member, a retracting side coupling member, a block coupling member, and an output functional member. The electric linear actuator is configured to reciprocate in a projecting direction and a retracting direction that define a movable direction. The output movable block and the counter movable block are arranged in parallel in a direction orthogonal to the movable direction. The block coupling member is coupled to the output movable block and the counter movable block. The output movable block and the counter movable block are reciprocated in opposite phases by electromagnetic force acting between the output movable block and the counter movable block. The output functional member is coupled to the block coupling member, and the output functional member includes a portion arranged further in the projecting direction than the block coupling member. The projecting side coupling member is arranged further in the projecting direction than the block coupling member and is coupled to the block coupling member. The retracting side coupling member is arranged further in the retracting direction than the block coupling member, and the retracing side coupling member is coupled to the block coupling member. The projecting side coupling member and the retracting side coupling member have different shapes.

Preferably, the projecting side coupling member is thinner than the retracting side coupling member.

The direction orthogonal to the movable direction in a plan view of the electric linear actuator is defined as a width direction. In this case, preferably, the projecting side coupling member has a shape that is asymmetrical to a center line in the width direction in a side view of the electric linear actuator.

Preferably, the electric linear actuator further includes a counter functional member. The counter functional member is coupled to the counter movable block.

In the electric linear actuator, the block coupling member preferably includes an output movable coupling portion, a counter movable coupling portion, a projecting side supporting portion, a retracting side supporting portion, an output side resin inlet portion, a counter side resin inlet portion, an output side resin flow path portion, and a counter side resin flow path portion. In this case, preferably, the output movable coupling portion, the counter movable coupling portion, the projecting side supporting portion, the retracting side supporting portion, the output side resin inlet portion, the counter side resin inlet portion, the output side resin flow path portion, and the counter side resin flow path portion are formed integrally from a resin material. In this structure, the output movable coupling portion is coupled to the output movable block. The counter movable coupling portion is coupled to the counter movable block. The projecting side supporting portion is coupled to the output movable coupling portion. The retracting side supporting portion is coupled to the counter movable coupling portion. The output side resin flow path portion is continuous with the output movable coupling portion. The counter side resin flow path portion is continuous with the counter movable coupling portion. The output side resin inlet portion is continuous with the output side resin flow path portion. The counter side resin inlet portion is continuous with the counter side resin flow path portion. The projecting side coupling member and the retracting side coupling member, which are formed integrally with the block coupling member from the resin material, are continuous with the output movable coupling portion and the counter movable coupling portion.

In the electric linear actuator, the block coupling member includes a coupling portion supporting surface that receives a load of the output shaft when coupled to a main body casing of the output shaft vibration-type electric device.

A further aspect of the present invention is an output shaft vibration-type electric device. The output shaft vibration-type electric device includes the electric linear actuator and the output shaft. The output shaft is coupled to the output functional member.

The output shaft vibration-type electric device is embodied in, for example, an electric oral hygiene device.

The electric linear actuator and the output shaft vibration-type electric device allow the driving efficiency to be increased.

DESCRIPTION OF THE EMBODIMENTS

First Embodiment

The structure of an output shaft vibration-type electric device 10 will now be described.

Figure 1:
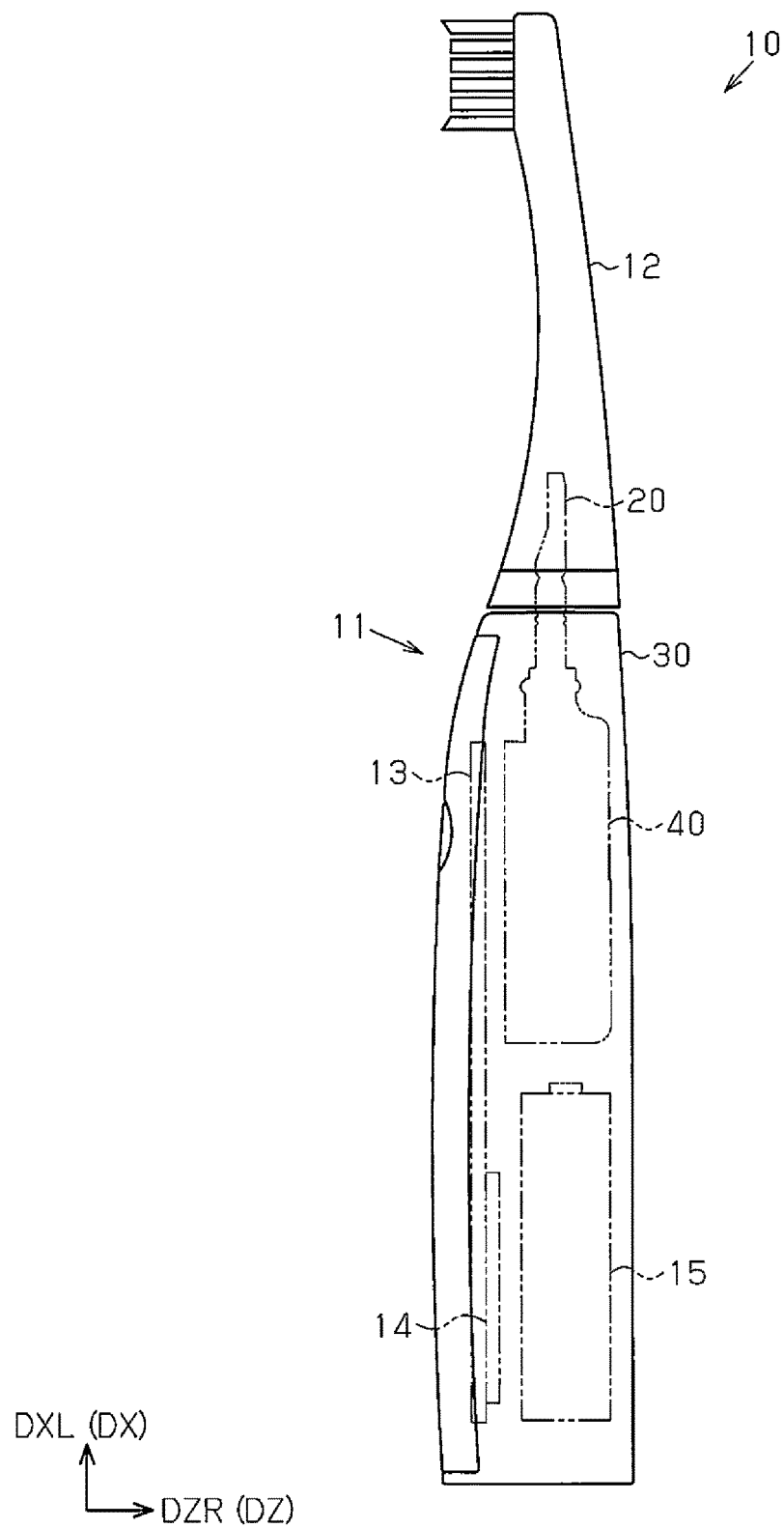
FIG. 1 is a front view of an output shaft vibration-type electric device in a first embodiment.
Figure 16:
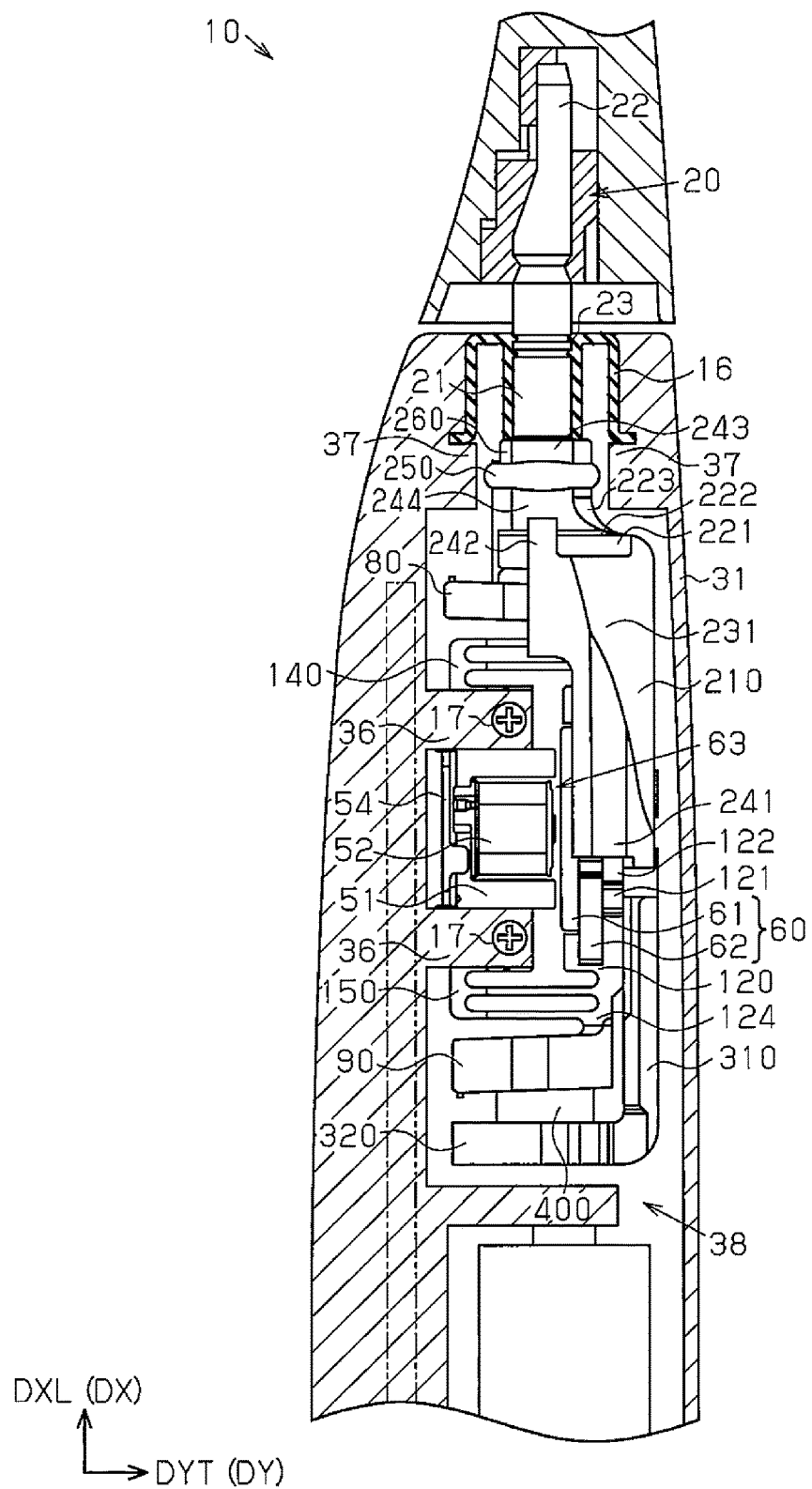
FIG. 16 is a partial cross-sectional view of the electric linear actuator in the first embodiment taken in a longitudinal direction.

The output shaft vibration-type electric device 10 will be described with reference to FIG. 1 and FIG. 16. For example, the output shaft vibration-type electric device 10 is embodied in an electric toothbrush as an electric oral hygiene device. The output shaft vibration-type electric device 10 includes a plurality of components. The plurality of components of the output shaft vibration-type electric device 10 include an electric device main body 11, a device functional member 12, a circuit board 13, a controller 14, a battery 15, an elastic member 16 (see FIG. 16), a fastening member 17 (see FIG. 16), and an electric linear actuator 40. The output shaft vibration-type electric device 10 has a structure in which the electric device main body 11 and the device functional member 12 can be coupled to and detached from each other. The output shaft vibration-type electric device 10 reciprocates the device functional member 12 with the electric linear actuator 40.

The electric device main body 11 has an elongated shape. The electric device main body 11 includes an output shaft 20 and a main body casing 30. The electric device main body 11 reciprocates the output shaft 20 with the electric linear actuator 40.

The main body casing 30 is formed from a resin material. The main body casing 30 has an elongated shape. The main body casing 30 includes a casing outer wall portion 31 and a casing inner space 38 (see FIG. 16). The casing inner space 38 is defined inside the casing outer wall portion 31 of the main body casing 30. The main body casing 30 includes the circuit board 13, the controller 14, the battery 15, and the electric linear actuator 40 that are incorporated in the casing inner space 38. The main body casing 30 incorporates a primary battery or a rechargeable battery as the battery 15. The main body casing 30 has a structure in which the battery 15 can be attached and detached.

The device functional member 12 is embodied in a toothbrush attachment. The device functional member 12 has an elongated shape. The device functional member 12 has a structure that can be coupled to and separated from the output shaft 20. The device functional member 12 reciprocates relative to the electric device main body 11 in accordance with the reciprocation of the output shaft 20. The device functional member 12 sets the output shaft vibration-type electric device 10 for use with an electric toothbrush.

The structure of the electric linear actuator 40 will now be described.

Figure 2:
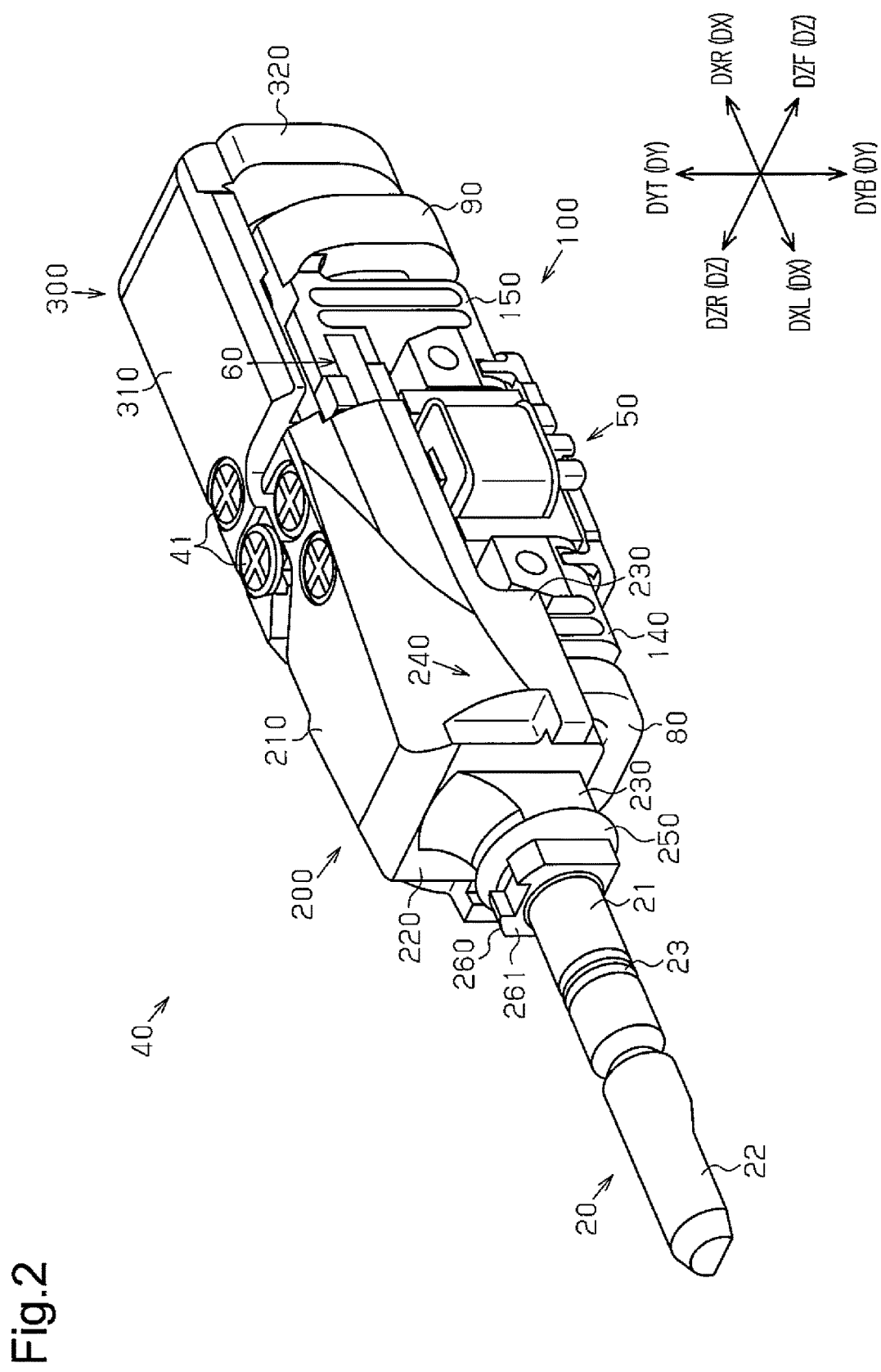
FIG. 2 is a perspective view of an electric linear actuator in the first embodiment.

The electric linear actuator 40 will be described with reference to FIG. 2. A movable direction DX, a height direction DY, a width direction DZ, and a planer direction are defined for components of the electric linear actuator 40. The movable direction DX is the two opposite directions of movement output by the electric linear actuator 40. The height direction DY is the two opposite directions orthogonal to the movable direction DX in a front view (FIG. 5) of the electric linear actuator 40. The width direction DZ is the two opposite directions orthogonal to the movable direction DX and the height direction DY. The planer direction is all directions orthogonal to the movable direction DX and thus includes the height direction DY and the width direction DZ.

One of the movable directions DX is a projecting direction DXL. The other movable direction DX is a retracting direction DXR. The projecting direction DXL is the direction in which the output shaft 20 is pushed out from the electric linear actuator 40 in the front view of the electric linear actuator 40. The retracting direction DXR is the direction in which the output shaft 20 is drawn into the electric linear actuator 40 in the front view of the electric linear actuator 40.

One of the height directions DY is a top surface direction DYT. The other height direction DY is a bottom surface direction DYB. The top surface direction DYT its the direction from a bottom side to a top side in the front view of the electric linear actuator 40. The bottom surface direction DYB indicates the direction from the top side to the bottom side in the front view of the electric linear actuator 40.

One of the width directions DZ is a front surface direction DZF. The other width direction DZ is a rear surface direction DZR. The front surface direction DZF is a direction from a rear surface side to a front surface side in a side view of the electric linear actuator 40. The rear surface direction DZR indicates a direction from the front surface side to the rear surface side in the side view of the electric linear actuator 40.

The electric linear actuator 40 is long in the movable direction DX. The electric linear actuator 40 is short in the width direction DZ. The electric linear actuator 40 includes a plurality of components. The plurality of components of the electric linear actuator 40 include a fixed block 50, an output movable block 60, a counter movable block 70, a projecting side coupling member 80, and a retracting side coupling member 90. The plurality of components of the electric linear actuator 40 further include a block coupling member 100, an output functional member 200, a counter functional member 300, an additional adjustment member 400, a plurality of fastening members 41, and a plurality of fastening members 42. The electric linear actuator 40 is coupled to the output shaft 20 by the output functional member 200. The electric linear actuator 40 reciprocates the output movable block 60 in the movable direction DX with electromagnetic force acting between the fixed block 50 and the output movable block 60. The electric linear actuator 40 outputs reciprocation in the movable direction DX through the reciprocation of the output movable block 60. The electric linear actuator 40 produces reciprocation in the movable direction DX to reciprocate the output shaft 20 in the movable direction DX.

The relationship of the components of the electric linear actuator 40 will now be described.

Figure 3:
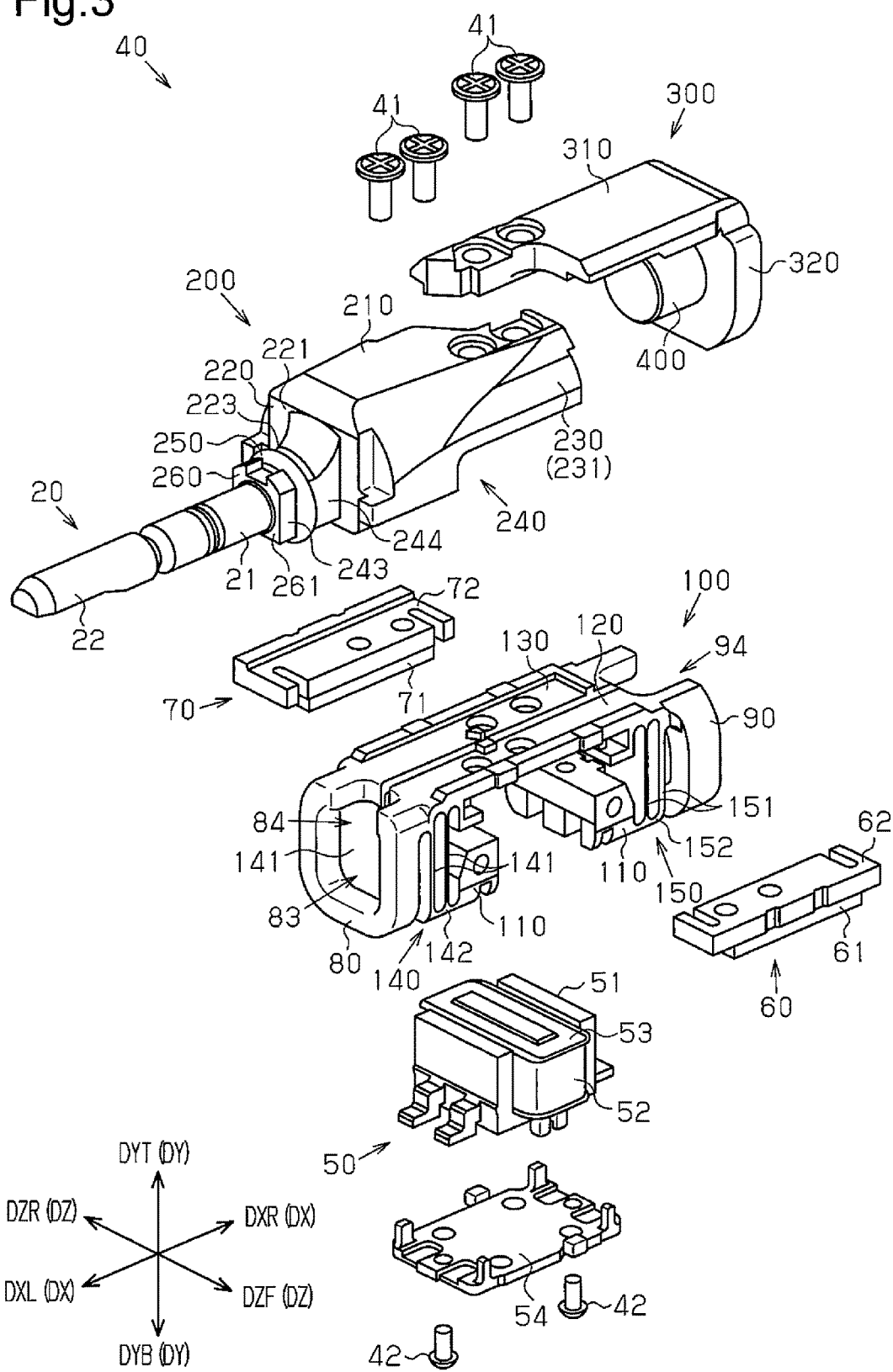
FIG. 3 is an exploded perspective view of the electric linear actuator in the first embodiment.

The relationship of the components will be described by mainly referring to FIG. 3. The electric linear actuator 40 includes a plurality of functional coupled portions that are integrated. The functional coupled portions are coupled to each other and integrated. Each functional coupled portion as a whole can move relative to another functional coupled portion. In the structure in which the functional coupled portions are integrated, the plurality of components in each functional coupled portion can move relative to each other. The fixed block 50, the output movable block 60, the counter movable block 70, the projecting side coupling member 80, and the retracting side coupling member 90 each serve as a functional coupled portion.

In the electric linear actuator 40, the output movable block 60 and the counter movable block 70 are arranged in parallel to each other in the width direction DZ. A gap is provided in between the output movable block 60 and the counter movable block 70 in the width direction DZ. The fixed block 50 and the output movable block 60 form a linear motor. The fixed block 50 and the counter movable block 70 form a linear motor. The output movable block 60 and the counter movable block 70 reciprocate in the movable direction DX in opposite phases.

The block coupling member 100 is coupled to the fixed block 50, the output movable block 60, the counter movable block 70, the projecting side coupling member 80, the retracting side coupling member 90, the output functional member 200, and the counter functional member 300. The block coupling member 100 enables the output movable block 60 and the counter movable block 70 to translate toward the fixed block 50.

The output shaft 20 is formed from a metal material. The output shaft 20 is arranged further in the projecting direction DXL than the block coupling member 100 in the movable direction DX. The output shaft 20 is coupled to the output functional member 200. The center line of the output shaft 20 is in parallel with the movable direction DX. The output shaft 20 includes a shaft base portion 21, a shaft distal end portion 22, and a fitting groove 23. The output shaft 20 is coupled to the output functional member 200 at the shaft base portion 21. The output shaft 20 is coupled to the device functional member 12 at the shaft distal end portion 22. The output shaft 20 reciprocates the device functional member 12 with the output from the electric linear actuator 40.

The structure of the fixed block 50 will now be described.

The fixed block 50 will be described with reference to FIG. 3 and FIGS. 5 to 7. The fixed block 50 is arranged at an intermediate portion of the block coupling member 100 in the movable direction DX. The fixed block 50 is arranged at a location on a side of the bottom surface direction DYB of an output movable coupling portion 120 and a counter movable coupling portion 130 in the height direction DY. The fixed block 50 is arranged from a portion on the side of the front surface direction DZF to a portion on the side of the rear surface direction DZR of the block coupling member 100 in the width direction DZ.

The fixed block 50 is block-shaped. The fixed block 50 is long in the movable direction DX. The fixed block 50 is short in the width direction DZ. The fixed block 50 includes a plurality of components. The plurality of components of the fixed block 50 include a core 51, a coil 52, an insulating member 53, and a supporting member 54. The fixed block 50 has a structure in which the plurality of components are coupled to each other. The plurality of components of the fixed block 50 are integrated, and thus form a single functional coupled portion. The fixed block 50 is coupled to a fixing coupling portion 110 of the block coupling member 100 with the plurality of fastening members 42. The fixed block 50 and the fixing coupling portion 110 are integrated.

The core 51 is formed from a magnetic material. The core 51 is block-shaped and includes a slit. The core 51 is arranged on a top surface of the supporting member 54. The core 51 is coupled to the supporting member 54. The core 51 has a maximum flux density suitable for resonantly driving the output movable block 60 and the counter movable block 70.

The coil 52 is formed from a conductive material. The coil 52 is wound around the core 51. The coil 52 is electrically connected to the circuit board 13 (see FIG. 1) through a lead line (not shown). The circuit board 13 supplies current to the coil 52. The number of windings of the coil 52 is suitable for reciprocating the output movable block 60 and the counter movable block 70.

The insulating member 53 is formed from a nonconductive material. The insulating member 53 is shaped to cover the teeth of the core 51. The insulating member 53 is coupled to the teeth of the core 51. The insulating member 53 is arranged between the core 51 and the coil 52 (see FIG. 7). The coil 52 and the core 51 are insulated from each other with the insulating member 53.

The supporting member 54 is formed from a resin material. The supporting member 54 has a shape similar to a flat plate shape. The supporting member 54 is arranged at a portion of the fixed block 50 on the side of the bottom surface direction DYB. The supporting member 54 is coupled to the fixing coupling portion 110 with the plurality of fastening members 42.

The structure of the output movable block 60 will now be described.

The output movable block 60 will be described with reference to FIG. 3, and FIGS. 5 to 7. The output movable block 60 is arranged between a projecting side supporting portion 140 and a retracting side supporting portion 150 in the movable direction DX. The output movable block 60 is arranged between the fixing coupling portion 110 and the output movable coupling portion 120 in the height direction DY. In the width direction DZ, the output movable block 60 is arranged at a portion further in the front surface direction DZF than the center line of the block coupling member 100 in the width direction DZ.

The output movable block 60 has a rectangular shape. The output movable block 60 includes a plurality of components. The plurality of components of the movable block 60 include an output permanent magnet 61 and an output back yoke 62. The output movable block 60 has a structure in which the plurality of components are coupled to each other. The plurality of components of the output movable block 60 are integrated. The output movable block 60 is coupled to the output movable coupling portion 120 of the block coupling member 100 with the plurality of fastening members 41. The output movable block 60 and the output movable coupling portion 120 are integrated.

The output permanent magnet 61 has a flat plate shape. The output permanent magnet 61 is coupled to the output back yoke 62 with an adhesive. The output permanent magnet 61 faces the fixed block 50 in the height direction DY (see FIG. 5). An output side gap 63 as a gap is formed between the output permanent magnet 61 and the fixed block 50. The output permanent magnet 61 is affected by a magnetic field formed by the fixed block 50 and thus moves in the movable direction DX relative to the fixed block 50. The output permanent magnet 61 moves in the movable direction DX in a phase opposite to that of the counter movable block 70.

The output back yoke 62 is formed from a magnetic material. The output back yoke 62 has a flat plate shape. The output back yoke 62 is coupled to the output movable coupling portion 120 of the block coupling member 100 with the plurality of fastening members 41. The output back yoke 62 increases absorption force or attraction force of the output permanent magnet 61.

The structure of the counter movable block 70 will now be described.

The counter movable block 70 will be described with reference to FIG. 3 and FIGS. 5 to 7. The counter movable block 70 is arranged between the projecting side supporting portion 140 and the retracting side supporting portion 150 in the movable direction DX. The counter movable block 70 is arranged between the fixing coupling portion 110 and the counter movable coupling portion 130 in the height direction DY. The counter movable block 70 is arranged at a portion further in the rear surface direction DZR than the center line of the block coupling member 100 in the width direction DZ, in the width direction DZ.

The counter movable block 70 has a rectangular shape. The counter movable block 70 includes a plurality of components. The plurality of components of the counter movable block 70 include a counter permanent magnet 71 and a counter back yoke 72. The counter movable block 70 has a structure in which the plurality of components are coupled to each other. The plurality of components of the counter movable block 70 are integrated. The counter movable block 70 is coupled to the counter movable coupling portion 130 of the block coupling member 100 with the plurality of fastening members 41. The counter movable block 70 and the counter movable coupling portion 130 are integrated.

The counter permanent magnet 71 has a flat plate shape. The counter permanent magnet 71 is coupled to the counter back yoke 72 with an adhesive. The counter permanent magnet 71 faces the fixed block 50 in the height direction DY (see FIG. 6). A counter side gap 73 is formed between the counter permanent magnet 71 and the fixed block 50. The counter permanent magnet 71 is affected by the magnetic field formed by the fixed block 50, and thus moves in the movable direction DX with respect to the fixed block 50. The counter permanent magnet 71 moves in the movable direction DX with a phase opposite to that of the output movable block 60.

The counter back yoke 72 is formed from a magnetic material. The counter back yoke 72 has a flat plate shape. The counter back yoke 72 is coupled to the counter movable coupling portion 130 of the block coupling member 100 with the plurality of fastening members 41. The counter back yoke 72 increases the absorption force or attraction force of the counter permanent magnet 71.

The structure of the projecting side coupling member 80 will now be described.

Figure 10:
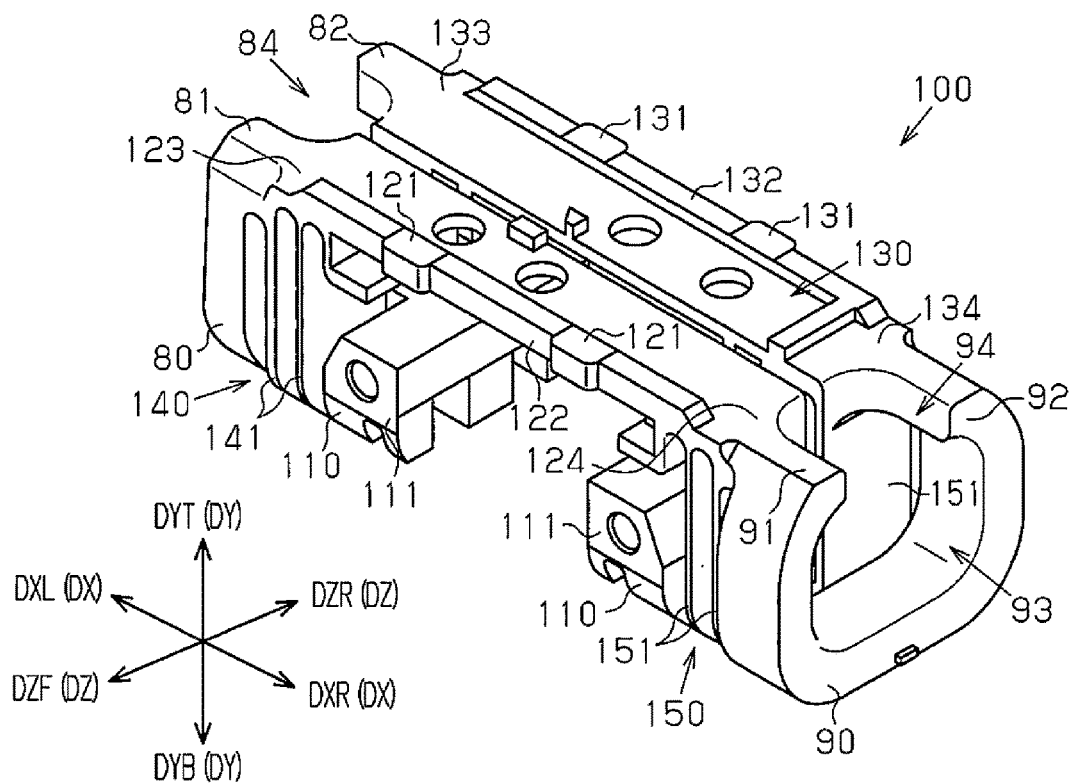
FIG. 10 is a perspective view of a block coupling member in the first embodiment.
Figure 11:
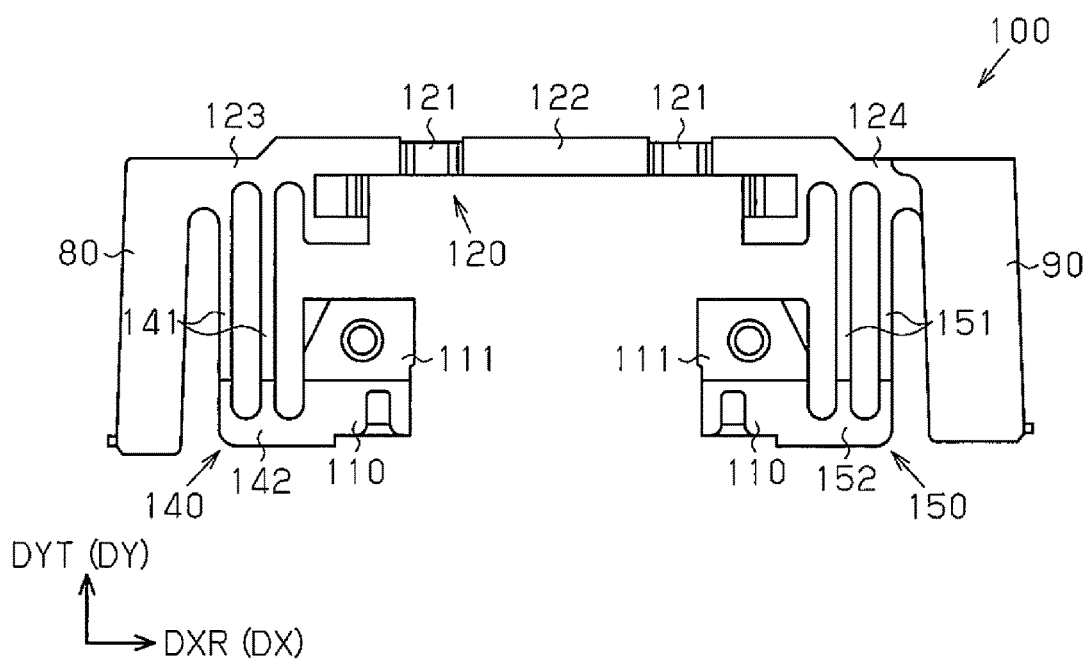
FIG. 11 is a front view of the block coupling member in the first embodiment.
Figure 12:
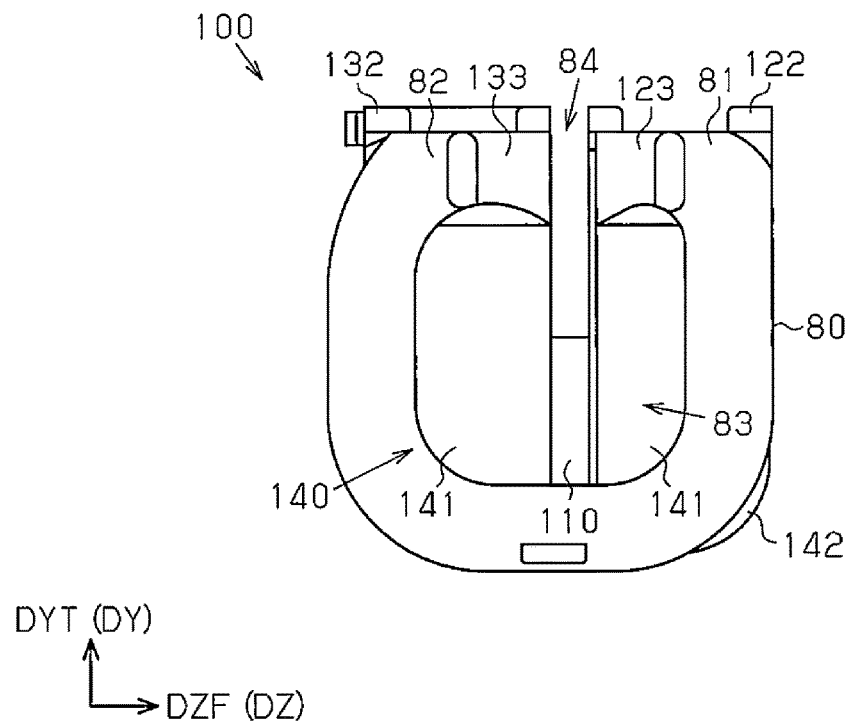
FIG. 12 is a side view of the block coupling member in the first embodiment at a projecting side.

The projecting side coupling member 80 will be described with reference to FIGS. 10 to 12. The projecting side coupling member 80 is arranged at a portion arranged further in the projecting direction DXL than the block coupling member 100 in the movable direction DX. In the height direction DY, the projecting side coupling member 80 is arranged from a portion of the block coupling member 100 on the side of the top surface direction DYT to a portion of the block coupling member 100 on the side of the bottom surface direction DYB. In the width direction DZ, the projecting side coupling member 80 is arranged from a portion of the block coupling member 100 on the side of the front surface direction DZF to a portion of the block coupling member 100 on the side of the rear surface direction DZR.

The projecting side coupling member 80 is formed from a resin material. The projecting side coupling member 80 has a shape similar to an annular shape. The projecting side coupling member 80 has a shape similar to a partially notched perfect annular shape, as an example of the shape similar to the annular shape. The projecting side coupling member 80 has an asymmetric shape with respect to the center line in the width direction DZ in a side view on the side of the projecting direction DXL. The projecting side coupling member 80 includes a coupling member output side end portion 81, a coupling member counter side end portion 82, a coupling member space 83, and a coupling member separation portion 84. The projecting side coupling member 80 can resonantly drive the output movable block 60 and the counter movable block 70.

The coupling member output side end portion 81 is coupled to the output movable coupling portion 120 of the block coupling member 100. The coupling member counter side end portion 82 is coupled to the counter movable coupling portion 130 of the block coupling member 100. The coupling member space 83 is formed at an inner side of the projecting side coupling member 80 having an annular shape or a shape similar to the annular shape. The coupling member separation portion 84 is arranged between the coupling member output side end portion 81 and the coupling member counter side end portion 82.

The structure of the retracting side coupling member 90 will now be described.

Figure 13:
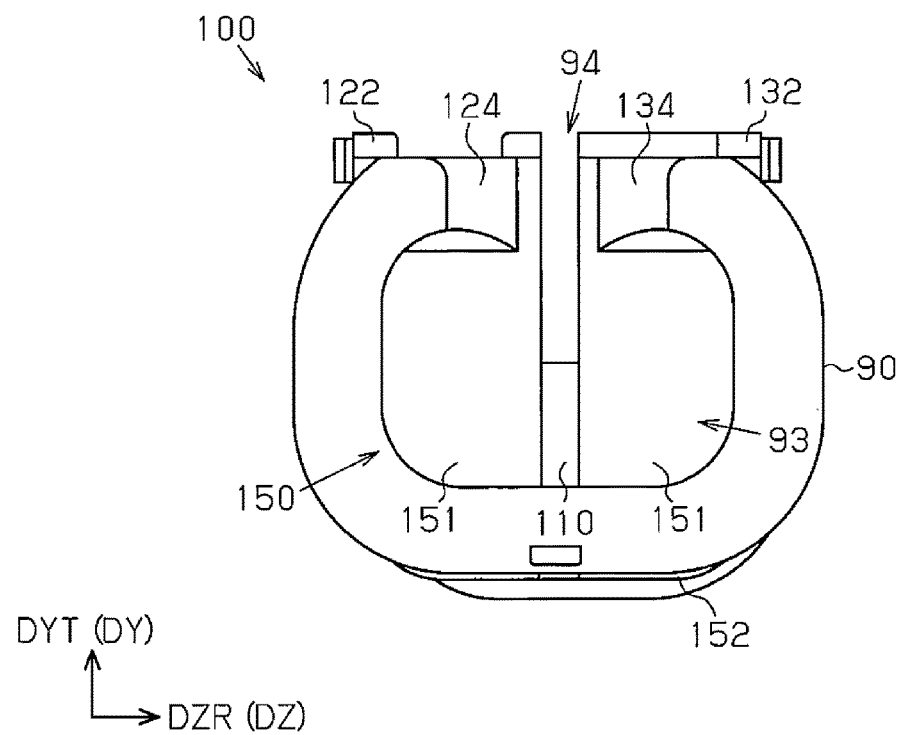
FIG. 13 is a side view of the block coupling member in the first embodiment at a retracting side.

The retracting side coupling member 90 will be described with reference to FIGS. 10, 11, and 13. The retracting side coupling member 90 is arranged at a portion further in the retracting direction DXR than the block coupling member 100 in the movable direction DX. In the height direction DY, the retracting side coupling member 90 is arranged from a portion of the block coupling member 100 on the side of the top surface direction DYT to a portion of the block coupling member 100 on the side of the bottom surface direction DYB. In the width direction DZ, the retracting side coupling member 90 is arranged from a portion of the block coupling member 100 on the side of the front surface direction DZF to a portion of the block coupling member 100 on the side of the rear surface direction DZR.

The retracting side coupling member 90 is formed from a resin material. The retracting side coupling member 90 has a shape similar to an annular shape. The retracting side coupling member 90 has a shape similar to a partially notched perfect annular shape, as an example of the shape similar to the annular shape. The retracting side coupling member 90 has a symmetrical shape with respect to the center line in the width direction DZ in a side view on the side of the projecting direction DXL. The retracting side coupling member 90 includes a coupling member output side end portion 91, a coupling member counter side end portion 92, a coupling member space 93, and a coupling member separation portion 94. The retracting side coupling member 90 can resonantly drive the output movable block 60 and the counter movable block 70.

The coupling member output side end portion 91 is coupled to the output movable coupling portion 120 of the block coupling member 100. The coupling member counter side end portion 92 is coupled to the counter movable coupling portion 130 of the block coupling member 100. The coupling member space 93 is formed on an inner side of the retracting side coupling member 90. The coupling member separation portion 94 is formed between the coupling member output side end portion 91 and the coupling member counter side end portion 92.

The coupling members 80 and 90 each have a structure based on the following design concept.

The projecting side coupling member 80 is arranged adjacent to the output functional member 200 in the movable direction DX. Thus, the projecting side coupling member 80 may come into contact with the output functional member 200 when the output movable block 60 and the counter movable block 70 reciprocate. Thus, the projecting side coupling member 80 has a coupling member contact prevention structure. With the coupling member contact prevention structure, the projecting side coupling member 80 is less likely to come into contact with the output functional member 200.

For example, as the coupling member contact prevention structure, the thickness of the projecting side coupling member 80 is within an appropriate thickness range. The appropriate thickness range of the projecting side coupling member 80 is, for example, smaller than the thickness of the retracting side coupling member 90. The thickness of the projecting side coupling member 80 can be defined by a distance between a surface on the side of the projecting direction DXL and a surface on the retracting side of the projecting side coupling member 80, in the movable direction DX. The thickness of the retracting side coupling member 90 can be defined by a distance between a surface on the side of the projecting direction DXL and a surface on the retracting side of the retracting side coupling member 90 in the movable direction DX.

The thickness of the projecting side coupling member 80 is smaller than the thickness of the retracting side coupling member 90. Thus, compared with when the thickness of the projecting side coupling member 80 is not smaller than the thickness of the retracting side coupling member 90, it is easier to provide a gap between the projecting side coupling member 80 and the output functional member 200. Thus, the thickness of the projecting side coupling member 80 within the appropriate thickness range contributes to the formation of the coupling member contact prevention structure.

The thickness of the projecting side coupling member 80 affects a spring constant of the projecting side coupling member 80. The spring constant of the projecting side coupling member 80 affects the resonant driving of the output movable block 60 and the counter movable block 70. Thus, the resonant driving may not be performed in a preferable manner, when the setting of the thickness of the projecting side coupling member 80 within the appropriate thickness range has a priority over the setting of a preferable spring constant of the projecting side coupling member 80. The preferable coupling member contact prevention structure is achieved with the smallest possible thickness of the projecting side coupling member 80. Thus, a design of improving the effect of the coupling member contact prevention structure leads to a smaller spring constant of the projecting side coupling member 80.

The resonant driving of the output movable block 60 and the counter movable block 70 is affected by the spring constant of the projecting side coupling member 80 and the spring constant of the retracting side coupling member 90. Thus, when the relationship between the thickness of the projecting side coupling member 80 and the appropriate thickness range has a high priority in the design, the preferable resonant driving can be performed by adjusting the thickness of the retracting side coupling member 90.

The projecting side coupling member 80 and the retracting side coupling member 90 have thicknesses based on the design concept described above. The thickness of the projecting side coupling member 80 contributes to the formation of the preferable coupling member contact prevention structure. The thickness of the retracting side coupling member 90 is larger than the thickness of projecting side coupling member 80. The thickness of the retracting side coupling member 90 compensates for the reduction of the spring constant of the projecting side coupling member 80 due to a small thickness of the projecting side coupling member 80. The retracting side coupling member 90 has a spring constant which forms the preferable resonant driving. The thickness of the retracting side coupling member 90 contributes to ensuring the spring constant. Thus, the preferable resonant driving is achieved by the spring constant of the projecting side coupling member 80 and the spring constant of the retracting side coupling member 90.

As described above, the projecting side coupling member 80 and the retracting side coupling member 90 have different shapes, and the preferable coupling member contact prevention structure and the preferable resonant driving are achieved.

The structure of the block coupling member 100 will now be described.

The block coupling member 100 will be described with reference to FIG. 10 and FIG. 11. The block coupling member 100 is formed from a resin material. The block coupling member 100 has a structure in which a plurality of components are formed integrally with the same resin material. The plurality of components of the block coupling member 100 include two fixing coupling portions 110, the output movable coupling portion 120, the counter movable coupling portion 130, two projecting side supporting portions 140, and two retracting side supporting portions 150. The plurality of components of the block coupling member 100 further include two output side resin inlet portions 121, an output side resin flow path portion 122, an output projecting side coupling portion 123, and an output retracting side coupling portion 124. The plurality of components of the block coupling member 100 include two counter side resin inlet portions 131, a counter side resin flow path portion 132, a counter projecting side coupling portion 133, and a counter retracting side coupling portion 134.

The block coupling member 100 includes a plurality of functional portions. Each functional portion as a whole can move relative to another functional portion. The fixing coupling portion 110, the output movable coupling portion 120, and the counter movable coupling portion 130 each serve as a functional portion.

In the movable direction DX, the fixing coupling portion 110 on the side of the projecting direction DXL is arranged at a portion further in the projecting direction DXL than the center line of the block coupling member 100 in the movable direction DX. In the movable direction DX, the fixing coupling portion 110 on the side of the retracting direction DXR is arranged at a portion further in the retracting direction DXR than the center line of the block coupling member 100 in the movable direction DX. Each fixing coupling portion 110 is arranged at a portion of the block coupling member 100 on the side of the bottom surface direction DYB in the height direction DY. In the width direction DZ, each fixing coupling portion 110 is arranged from a portion of the block coupling member 100 on the side of the front surface direction DZF to a portion of the block coupling member 100 on the side of the rear surface direction DZR.

Each fixing coupling portion 110 is block-shaped. The fixing coupling portion 110 on the side of the projecting direction DXL and the fixing coupling portion 110 on the side of the retracting direction DXR face each other in the movable direction DX. The fixing coupling portion 110, on the side of the projecting direction DXL, is continuous with the projecting side supporting portion 140. The fixing coupling portion 110, on the side of the retracting direction DXR, is continuous with the retracting side supporting portion 150. Each fixing coupling portion 110 has a structure for holding the fixed block 50. Each fixing coupling portion 110 has a coupling portion supporting surface 111. The coupling portion supporting surface 111 has a flat surface shape.

The output movable coupling portion 120 is arranged between the projecting side coupling member 80 and the retracting side coupling member 90 in the movable direction DX. In the height direction DY, the output movable coupling portion 120 is arranged at a portion of the block coupling member 100 on the side of the top surface direction DYT. In the width direction DZ, the output movable coupling portion 120 is arranged at a portion further in the front surface direction DZF than the center line of the block coupling member 100 in the width direction DZ.

The output movable coupling portion 120 is formed integrally with two output side resin inlet portions 121, an output side resin flow path portion 122, an output projecting side coupling portion 123, and an output retracting side coupling portion 124. The output movable coupling portion 120, the two output side resin inlet portions 121, the output side resin flow path portion 122, the output projecting side coupling portion 123, and the output retracting side coupling portion 124 form a single functional portion.

The output side resin inlet portion 121 has a rectangular shape. The output side resin inlet portion 121 is long in the movable direction DX. The output side resin inlet portion 121 is formed on the output side resin flow path portion 122. The output side resin inlet portion 121 on the side of the projecting direction DXL and the output side resin inlet portion 121 on the side of the retracting direction DXR are arranged in the movable direction DX with a gap in between.

The output side resin flow path portion 122 has a rectangular shape longer than the output side resin inlet portion 121. The output side resin flow path portion 122 is long in the movable direction DX. The output side resin flow path portion 122 is formed on the output movable coupling portion 120. The output side resin flow path portion 122 is arranged from an end portion of the output movable coupling portion 120 on the side of the projecting direction DXL to an end portion of the output movable coupling portion 120 on the side of the retracting direction DXR.

The output projecting side coupling portion 123 has a shape similar to a flat plate shape. The output projecting side coupling portion 123 is long in the width direction DZ. The output projecting side coupling portion 123 is continuous with the end portion of the output side resin flow path portion 122 on the side of the projecting direction DXL. The output projecting side coupling portion 123 couples the output side resin flow path portion 122, the projecting side supporting portion 140, and the projecting side coupling member 80 to one another. A top portion of the output projecting side coupling portion 123 has a flat surface shape. The flat surface shape of the output projecting side coupling portion 123 contributes to the smooth flow of a resin material from the output side resin flow path portion 122 to the projecting side supporting portion 140 and the projecting side coupling member 80 when the block coupling member 100 is molded.

The output retracting side coupling portion 124 has a shape similar to a flat plate shape. The output retracting side coupling portion 124 is long in the width direction DZ. The output retracting side coupling portion 124 is continuous with the end portion of the output side resin flow path portion 122 on the side of the retracting direction DXR. The output retracting side coupling portion 124 couples the output side resin flow path portion 122, the retracting side supporting portion 150, and the retracting side coupling member 90 are coupled to one another. A top portion of the output retracting side coupling portion 124 has a flat surface shape. The flat surface shape of the output retracting side coupling portion 124 contributes to the smooth flow of a resin material from the output side resin flow path portion 122 to the retracting side supporting portion 150 and the retracting side coupling member 90 when the block coupling member 100 is molded.

The counter movable coupling portion 130 is arranged between the projecting side coupling member 80 and the retracting side coupling member 90 in the movable direction DX. The counter movable coupling portion 130 is arranged at a portion of the block coupling member 100 on the side of the top surface direction DYT in the height direction DY. In the width direction DZ, the counter movable coupling portion 130 is arranged at a portion further in the rear surface direction DZR than the center line of the block coupling member 100 in the width direction DZ.

The counter movable coupling portion 130 is formed integrally with the two counter side resin inlet portions 131, the counter side resin flow path portion 132, the counter projecting side coupling portion 133, and the counter retracting side coupling portion 134. The counter movable coupling portion 130, the two counter side resin inlet portions 131, the counter side resin flow path portion 132, the counter projecting side coupling portion 133, and the counter retracting side coupling portion 134 form a single functional portion.

The counter side resin inlet portion 131 has a rectangular shape. The counter side resin inlet portion 131 is long in the movable direction DX. The counter side resin inlet portion 131 is formed on the counter side resin flow path portion 132. The counter side resin inlet portion 131 on the side of the projecting direction DXL and the counter side resin inlet portion 131 on the side of the retracting direction DXR are formed in the movable direction DX with a gap in between.

The counter side resin flow path portion 132 has a rectangular shape that is longer than the counter side resin inlet portion 131. The counter side resin flow path portion 132 is long in the movable direction DX. The counter side resin flow path portion 132 is formed on the counter movable coupling portion 130. The counter side resin flow path portion 132 is arranged from an end portion of the counter movable coupling portion 130 on the side of the projecting direction DXL to an end portion of the counter movable coupling portion 130 on the side of the retracting direction DXR.

The counter projecting side coupling portion 133 has a shape similar to a flat plate shape. The counter projecting side coupling portion 133 is long in the width direction DZ. The counter projecting side coupling portion 133 is continuous with an end portion of the counter side resin flow path portion 132 on the side of the projecting direction DXL. The counter projecting side coupling portion 133 couple the counter side resin flow path portion 132, the projecting side supporting portion 140, and the projecting side coupling member 80 to one another. A top portion of the counter projecting side coupling portion 133 has a flat surface shape. The flat surface shape of the counter projecting side coupling portion 133 contributes to a smooth flow of a resin material from the counter side resin flow path portion 132 to the projecting side supporting portion 140 and the projecting side coupling member 80 when the block coupling member 100 is molded.

The counter retracting side coupling portion 134 has a shape similar to a flat plate shape. The counter retracting side coupling portion 134 is long in the width direction DZ. The counter retracting side coupling portion 134 is continuous with an end portion of the counter side resin flow path portion 132 on the side of the retracting direction DXR. The counter projecting side coupling portion 133 couples the counter side resin flow path portion 132, the retracting side supporting portion 150, and the retracting side coupling member 90 to one another. A top portion of the counter retracting side coupling portion 134 has a flat surface shape. The flat surface shape of the counter retracting side coupling portion 134 contributes to a smooth flow of a resin material from the counter side resin flow path portion 132 to the retracting side supporting portion 150 and the retracting side coupling member 90 when the block coupling member 100 is molded.

The structure of the projecting side supporting portion 140 will now be described.

The projecting side supporting portion 140 will be described with reference to FIGS. 3, 7, 11, and 12. The projecting side supporting portion 140 is arranged between the fixing coupling portion 110 on the side of the projecting direction DXL and the projecting side coupling member 80 in the movable direction DX. The projecting side supporting portion 140 includes a projecting side deformation portion 141 and a projecting side coupling portion 142.

The projecting side supporting portion 140 on the side of the front surface direction DZF is arranged at a portion on the side of the bottom surface direction DYB of the output projecting side coupling portion 123 in the height direction DY. In the width direction DZ, the projecting side supporting portion 140 on the side of the front surface direction DZF is arranged at a portion further in the front surface direction DZF than the center line of the block coupling member 100 in the width direction DZ.

The projecting side supporting portion 140 on the side of the rear surface direction DZR is arranged at a portion on the side of the bottom surface direction DYB on the counter projecting side coupling portion 133 in the height direction DY. In the width direction DZ, the projecting side supporting portion 140 on the side of the rear surface direction DZR is arranged at a portion further in the rear surface direction DZR than the center line of the block coupling member 100 in the width direction DZ.

The projecting side deformation portion 141 has a thin plate shape. The projecting side deformation portion 141 is long in the height direction DY. The projecting side deformation portion 141 is short in the width direction DZ. The projecting side deformation portion 141 has a deformation amount in the longitudinal direction smaller than a deformation amount in the movable direction DX. The projecting side deformation portions 141 deform independently from each other in the movable direction DX.

The projecting side deformation portion 141 on the side of the front surface direction DZF is coupled to the output projecting side coupling portion 123. In the height direction DY, the projecting side deformation portion 141 on the side of the front surface direction DZF defines a position of a portion of the output movable coupling portion 120 on the side of the projecting direction DXL corresponding to the fixing coupling portion 110. The projecting side deformation portion 141 on the side of the front surface direction DZF enables the output movable block 60 to translate toward the fixed block 50 in the movable direction DX.

The projecting side deformation portion 141 on the side of the rear surface direction DZR is coupled to the counter projecting side coupling portion 133. The projecting side deformation portion 141 on the side of the rear surface direction DZR defines a position of a portion of the counter movable coupling portion 130 on the side of the projecting direction DXL corresponding to the fixing coupling portion 110 in the height direction DY. The projecting side deformation portion 141 on the side of the rear surface direction DZR enables the counter movable block 70 to translate toward the fixed block 50 in the movable direction DX.

The projecting side coupling portion 142 has a rectangular shape. The fixing coupling portion 110 on the side of the projecting direction DXL and the projecting side deformation portion 141 on the side of the front surface direction DZF are coupled to each other by the projecting side coupling portion 142 on the side of the front surface direction DZF. The projecting side coupling portion 142 on the side of the rear surface direction DZR couples the fixing coupling portion 110 on the side of the projecting direction DXL and the projecting side deformation portion 141 on the side of the rear surface direction DZR.

The structure of the retracting side supporting portion 150 will now be described.

The retracting side supporting portion 150 will be described with reference to FIGS. 3, 7, 10, and 13. The retracting side supporting portion 150 is arranged between the fixing coupling portion 110 on the side of the retracting direction DXR and the retracting side coupling member 90 in the movable direction DX. The retracting side supporting portion 150 includes a retracting side deformation portion 151 and a retracting side coupling portion 152.

The retracting side supporting portion 150 on the side of the front surface direction DZF is arranged at a portion on the side of the bottom surface direction DYB of the output retracting side coupling portion 124 in the height direction DY. In the width direction DZ, the retracting side supporting portion 150 on the side of the front surface direction DZF is arranged at a portion further in the front surface direction DZF than the center line of the block coupling member 100 in the width direction DZ.

The retracting side supporting portion 150 on the side of the rear surface direction DZR is arranged at a portion on the side of the bottom surface direction DYB of the counter retracting side coupling portion 134 in the height direction DY. In the width direction DZ, the retracting side supporting portion 150 on the side of the rear surface direction DZF is arranged at a portion further in the rear surface direction DZR than the center line of the block coupling member 100 in the width direction DZ.

The retracting side deformation portion 151 has a thin plate shape. The retracting side deformation portion 151 is long in the height direction DY. The retracting side deformation portion 151 is short in the width direction DZ. The retracting side deformation portion 151 has a deformation amount in the longitudinal direction smaller than a deformation amount in the movable direction DX. The retracting side deformation portions 151 deform independently from each other in the movable direction DX.

The retracting side deformation portion 151 on the side of the front surface direction DZF is coupled to the output retracting side coupling portion 124. The retracting side deformation portion 151 on the side of the front surface direction DZF defines a position of a portion of the output movable coupling portion 120 on the side of the retracting direction DXR corresponding to the fixing coupling portion 110 in the height direction DY. The retracting side deformation portion 151 on the side of the front surface direction DZF enables the output movable block 60 to translate toward the fixed block 50 in the movable direction DX.

The retracting side deformation portion 151 on the side of the rear surface direction DZR is coupled to the counter retracting side coupling portion 134. The retracting side deformation portion 151 on the side of the rear surface direction DZR defines a position of a portion of the counter movable coupling portion 130 on the side of the retracting direction DXR corresponding to the fixing coupling portion 110 in the height direction DY. The retracting side deformation portion 151 on the side of the rear surface direction DZR enables the counter movable block 70 to translate toward the fixed block 50 in the movable direction DX.

The retracting side coupling portion 152 has a rectangular shape. The retracting side coupling portion 152 on the side of the front surface direction DZF couples the fixing coupling portion 110 on the side of the retracting direction DXR and the retracting side deformation portion 151 on the side of the front surface direction DZF to each other. The retracting side coupling portion 152 on the side of the rear surface direction DZR couples the fixing coupling portion 110 on the side of the retracting direction DXR and the retracting side deformation portion 151 on the side of the rear surface direction DZR to each other.

The projecting side supporting portion 140 and the retracting side supporting portion 150 have the following functions.

The projecting side supporting portion 140 on the side of the front surface direction DZF and the retracting side supporting portion 150 on the side of the front surface direction DZF each define the position of the output movable block 60 relative to the fixed block 50 in the height direction DY. The output side gap 63 is formed with the position of the output movable block 60 in the height direction DY defined by the projecting side supporting portion 140 on the side of the front surface direction DZF and the retracting side supporting portion 150 on the side of the front surface direction DZF.

The projecting side supporting portion 140 on the side of the rear surface direction DZR and the retracting side supporting portion 150 on the side of the rear surface direction DZR each define the position of the counter movable block 70 relative to the fixed block 50 in the height direction DY. The counter side gap 73 is formed with the position of the counter movable block 70 in the height direction DY defined by the projecting side supporting portion 140 on the side of the rear surface direction DZR and the retracting side supporting portion 150 on the side of the rear surface direction DZR.

The projecting side deformation portion 141 on the side of the front surface direction DZF and the retracting side deformation portion 151 on the side of the front surface direction DZF limit the movement direction of the output movable block 60 relative to the fixed block 50 to the movable direction DX. Thus, the output movable block 60 translates in the movable direction DX due to the electromagnetic force acting between the output movable block 60 and the fixed block 50.

The projecting side deformation portion 141 on the side of the rear surface direction DZR and the retracting side deformation portion 151 on the side of the rear surface direction DZR limit the movement direction of the counter movable block 70 relative to the fixed block 50 to the movable direction DX. Thus, the counter movable block 70 translates in the movable direction DX due to the electromagnetic force acting between the counter movable block 70 and the fixed block 50.

The structure of the output functional member 200 will now be described.

The output functional member 200 will be described with reference to FIGS. 3 to 5, 7, and 8. The output functional member 200 is arranged at a portion further in the projecting direction DXL than the counter functional member 300 in the movable direction DX. The output functional member 200 is arranged at a portion further in the top surface direction DYT than the block coupling member 100 in the height direction DY. In the width direction DZ, the output functional member 200 is arranged from a portion of the block coupling member 100 on the side of the front surface direction DZF to a portion of the block coupling member 100 on the side of the rear surface direction DZR.

The output functional member 200 is formed from a resin material. The output functional member 200 is long in the movable direction DX. The output functional member 200 is short in the width direction DZ. The output functional member 200 is coupled to the output movable coupling portion 120 with the plurality of fastening members 41. The output functional member 200 and the output movable coupling portion 120 are integrated. The output functional member 200 includes a plurality of components formed integrally from the same resin material. The plurality of components of the output functional member 200 include an output member main body portion 210, an output shaft coupling portion 220, an output member reinforcement portion 230, an inner structure protecting portion 240, a load receiving portion 250, and a member receiving portion 260.

The output member main body portion 210 has a flat plate shape. The output member main body portion 210 is arranged on the top surfaces of the output movable coupling portion 120 and the counter movable coupling portion 130. The output member main body portion 210 is coupled to the output movable coupling portion 120 with the plurality of fastening members 41. The output member main body portion 210 forms a base portion of the output functional member 200.

The output shaft coupling portion 220 is arranged at a portion further in the projecting direction DXL than the projecting side coupling member 80 in the movable direction DX. The output shaft coupling portion 220 is continuous with the output member main body portion 210 and the output member reinforcement portion 230. The output shaft coupling portion 220 includes a coupling portion base portion 221, a coupling portion base surface 222, a coupling portion outer wall portion 223, and a coupling portion inner space 224.

The coupling portion base portion 221 has a flat plate shape. The coupling portion base portion 221 is continuous with an end portion of the output member main body portion 210 on the side of the projecting direction DXL and an end portion of the output member reinforcement portion 230 on the side of the projecting direction DXL. A gap is formed between the coupling portion base portion 221 and the projecting side coupling member 80. The coupling portion base portion 221 faces the projecting side supporting portion 140 in the movable direction DX with the coupling member space 83 arranged therebetween.

The coupling portion base surface 222 has a flat surface shape. The coupling portion base surface 222 is formed at a portion of the coupling portion base portion 221 on the side of the projecting direction DXL. The coupling portion base surface 222 is parallel to the planer direction.

The coupling portion outer wall portion 223 has a cylindrical shape. The coupling portion outer wall portion 223 is continuous with the coupling portion base portion 221. The coupling portion outer wall portion 223 projects in the projecting direction DXL from the coupling portion base surface 222. The coupling portion outer wall portion 223 defines the coupling portion inner space 224 (see FIG. 7). The coupling portion outer wall portion 223 accommodates the shaft base portion 21 in the coupling portion inner space 224. The coupling portion outer wall portion 223 is coupled to the shaft base portion 21. The coupling portion outer wall portion 223 surrounds an outer circumference of the shaft base portion 21.

The output member reinforcement portion 230 is continuous with the output member main body portion 210. The output member reinforcement portion 230 includes an output side reinforcement portion 231 and a counter side reinforcement portion 232. The output member reinforcement portion 230 reinforces the output member main body portion 210, the output shaft coupling portion 220, and a connection portion between the output member main body portion 210 and the output shaft coupling portion 220. The output member reinforcement portion 230 has a gap checking structure and a reinforcement portion contact prevention structure.

In the movable direction DX, the output side reinforcement portion 231 is arranged from an end portion of the output member main body portion 210 on the side of the retracting direction DXR to an end portion of the output member main body portion 210 on the side of the projecting direction DXL. The output side reinforcement portion 231 is arranged at a portion further in the front surface direction DZF than the block coupling member 100 in the width direction DZ. The output side reinforcement portion 231 is continuous with a portion of the output member main body portion 210 on the side of the front surface direction DZF.

The counter side reinforcement portion 232 is arranged at a portion on the side of the projecting direction DXL of the output member main body portion 210 in the movable direction DX. The counter side reinforcement portion 232 is arranged at a portion on the side of the rear surface direction DZR of the block coupling member 100 in the width direction DZ. The counter side reinforcement portion 232 is continuous with a portion of the output member main body portion 210 on the side of the rear surface direction DZR.

The gap checking structure will now be described.

Figure 5:
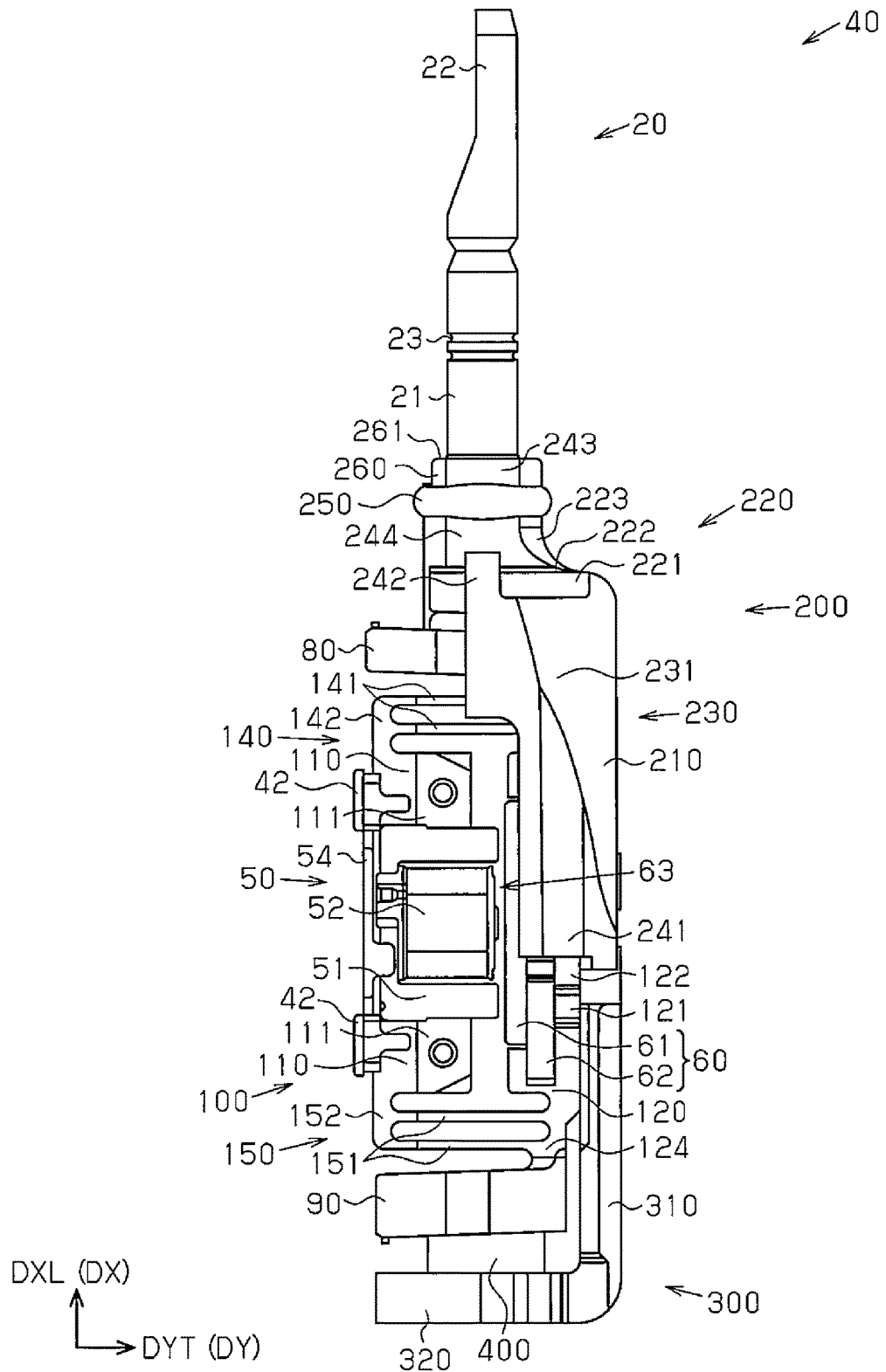
FIG. 5 is a front view of the electric linear actuator in the first embodiment.
Figure 6:
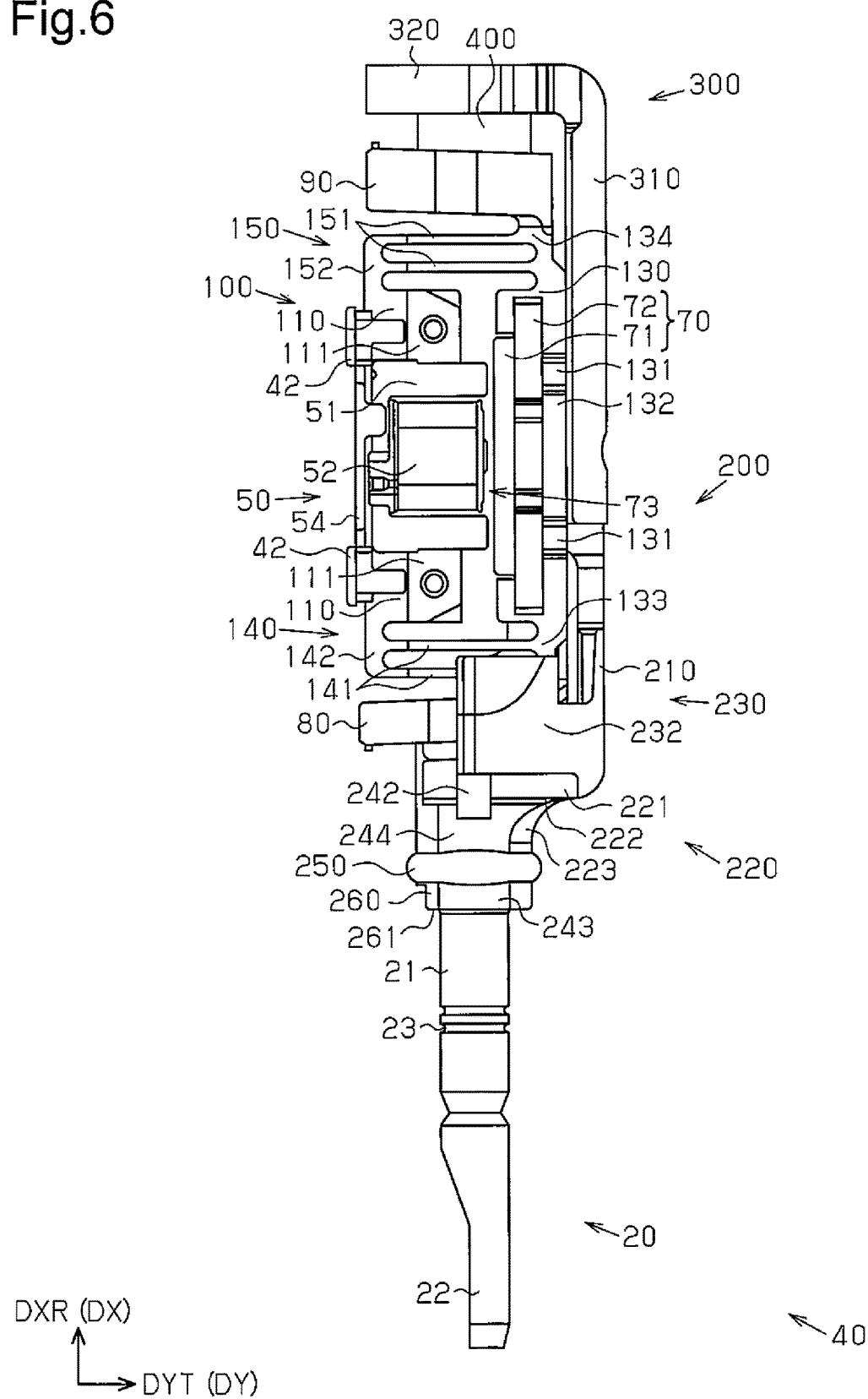
FIG. 6 is a rear view of the electric linear actuator in the first embodiment.
Figure 7:
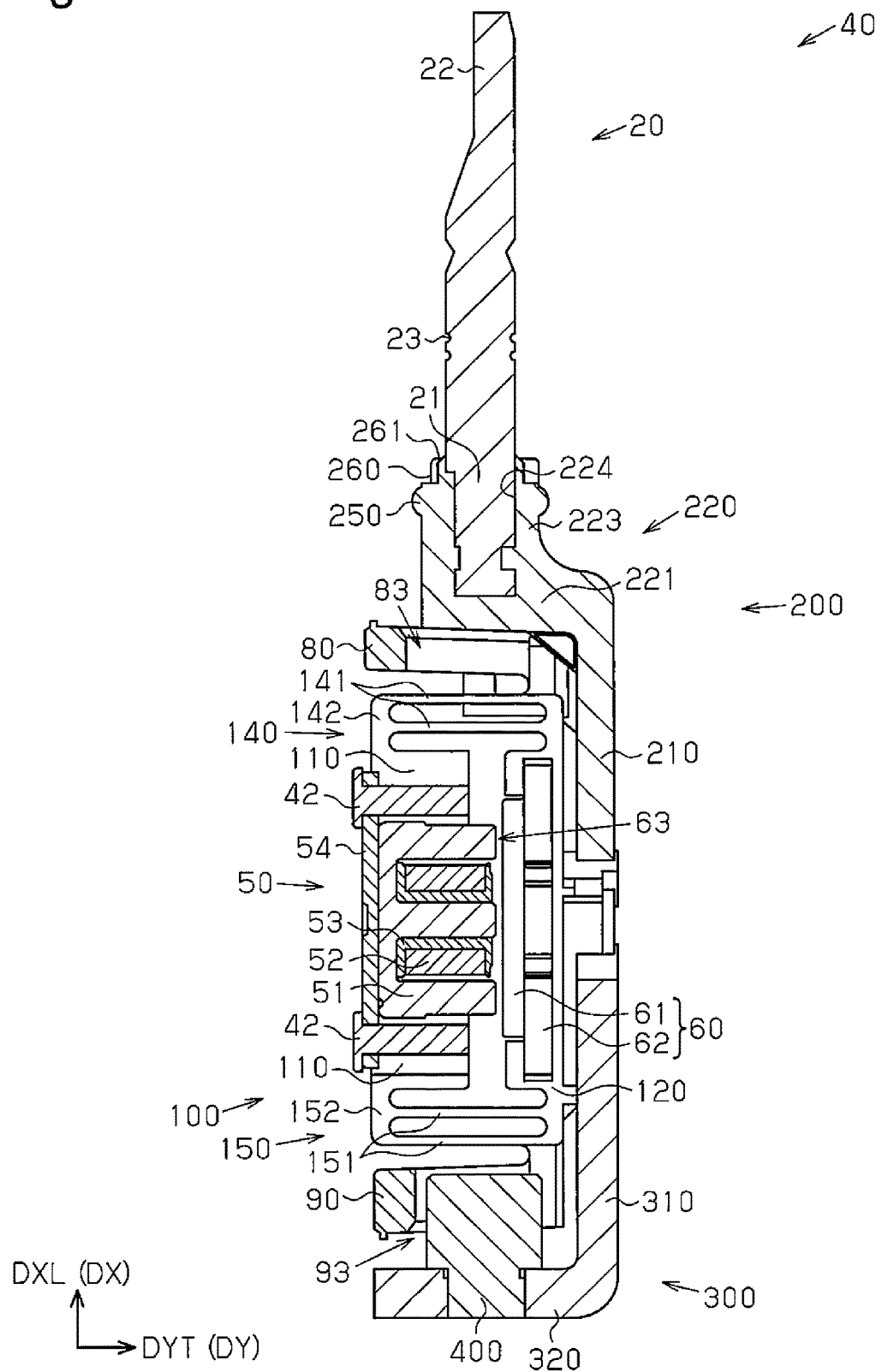
FIG. 7 is a cross-sectional view of the electric linear actuator in the first embodiment taken along line XA-XA in FIG. 4.
Figure 8:
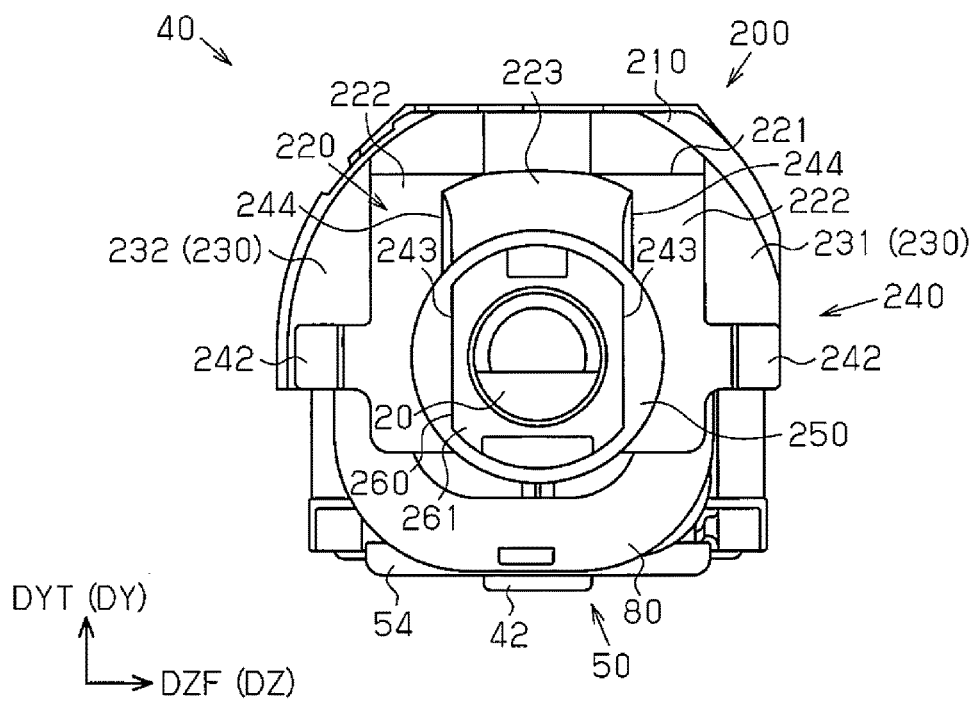
FIG. 8 is a side view of the electric linear actuator in the first embodiment at a projecting direction side.
Figure 9:
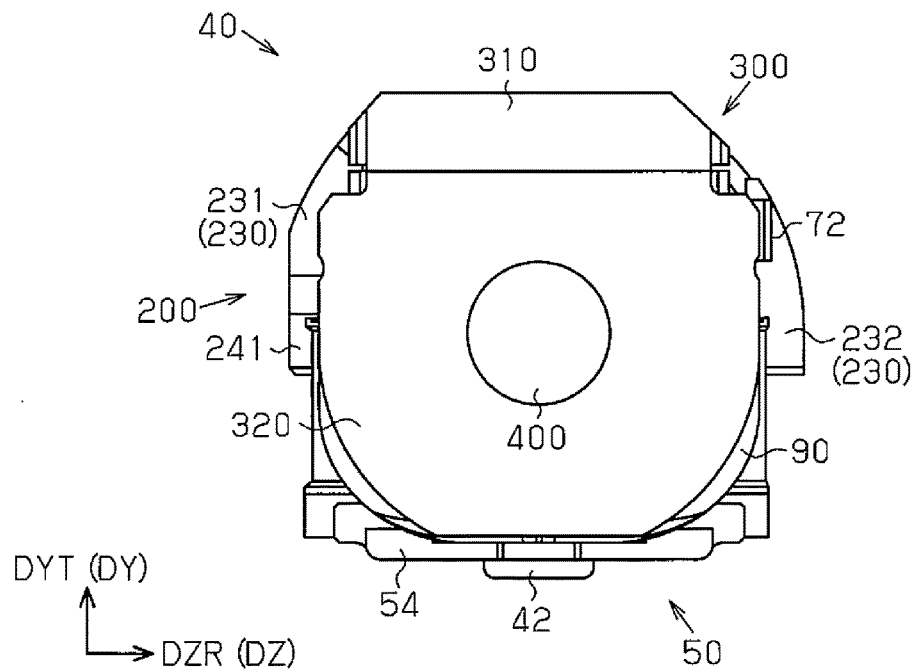
FIG. 9 is a side vide of the electric linear actuator in the first embodiment at a retracting direction side.

The gap checking structure is described mainly based on FIGS. 5 and 6. The gap checking structure includes an output side gap checking structure for checking the output side gap 63 (FIG. 5) and a counter side gap checking structure for checking the counter side gap 73 (FIG. 6). When there is no output side gap checking structure, it is difficult to check the size and the shape of the output side gap 63 after the output functional member 200 is coupled to the block coupling member 100 in a manufacturing step. When there is no counter side gap checking structure, it is difficult to check the size and the shape of the counter side gap 73 after the counter functional member 300 is coupled to the block coupling member 100 in a manufacturing step.

The output side gap checking structure exposes the output side gap 63 to the outside of the electric linear actuator 40 in a front view of the electric linear actuator 40. For example, in the output side gap checking structure, an edge of the output side reinforcement portion 231 adjacent to the output movable block 60 is formed at a portion further in the top surface direction DYT than the output side gap 63. Thus, the output side gap checking structure improves the efficiency for checking the output side gap 63 after the output functional member 200 is coupled to the block coupling member 100.

The counter side gap checking structure exposes the counter side gap 73 to the outside of the electric linear actuator 40 in a rear view of the electric linear actuator 40. For example, in the counter side gap checking structure, the counter side reinforcement portion 232 is not arranged adjacent to the counter movable block 70. Thus, the counter side gap checking structure improves the efficiency for checking the counter side gap 73 after the counter functional member 300 is coupled to the block coupling member 100.

The reinforcement portion contact prevention structure will now be described.

Figure 4:
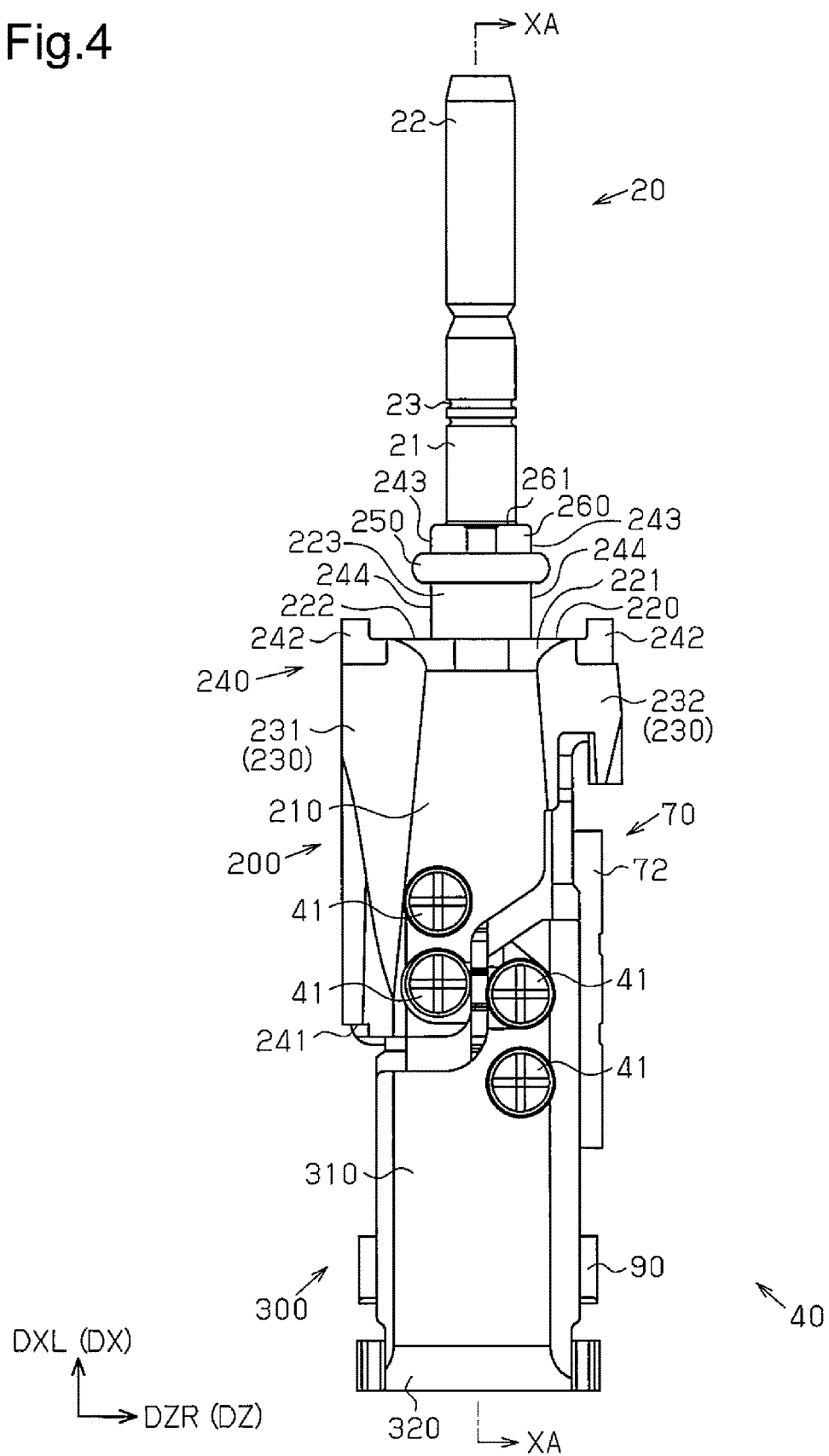
FIG. 4 is a plan view of the electric linear actuator in the first embodiment.

The reinforcement portion contact prevention structure will be described with reference to FIGS. 4 to 6. In the electric linear actuator 40, if there is no reinforcement portion contact prevention structure, the counter side reinforcement portion 232 may come into contact with at least one of the counter movable block 70 and the counter movable coupling portion 130 due to the reasons described below.

The counter side reinforcement portion 232 is integrated with the output movable block 60 and the output movable coupling portion 120. Thus, the counter side reinforcement portion 232 moves in a phase that is the same as that of the output movable block 60 and the output movable coupling portion 120. The counter side reinforcement portion 232 moves in a phase opposite to that of the counter movable block 70 and the counter movable coupling portion 130. Thus, when moving in the movable direction DX, the counter side reinforcement portion 232 may come into contact with at least one of the counter movable block 70 and the counter movable coupling portion 130.

The reinforcement portion contact prevention structure prevents the counter side reinforcement portion 232 from coming into contact with the counter movable block 70 and the counter movable coupling portion 130. For example, the reinforcement portion contact prevention structure has a length of the counter side reinforcement portion 232 within an appropriate length range. For example, in the movable direction DX, the length of the counter side reinforcement portion 232 can be defined by a distance between an end portion of the counter side reinforcement portion 232 on the side of the projecting direction DXL to an end portion of the counter side reinforcement portion 232 on the side of the retracting direction DXR.

For example, the reinforcement portion contact prevention structure has, as the length within the appropriate length range, a length of the counter side reinforcement portion 232 shorter than the length of the output side reinforcement portion 231. The reinforcement portion contact prevention structure has, as an example of the length, a length from the coupling portion base portion 221 to a portion further in the projecting direction DXL than the counter movable block 70. The reinforcement portion contact prevention structure has, as an example of the length, a length from the coupling portion base portion 221 to a portion adjacent to the projecting side coupling member 80.

The reinforcement portion contact prevention structure has the following advantage. The counter side reinforcement portion 232 has a length within the appropriate length range. Thus, a space (hereinafter, referred to as "contact prevention space") between the counter movable block 70 and the counter movable coupling portion 130 is formed. The counter side reinforcement portion 232 has a length shorter than the length of the output side reinforcement portion 231 so that a larger contact prevention space is formed. The counter side reinforcement portion 232 has a length from the coupling portion base portion 221 to a portion further in the projecting direction DXL than the counter movable block 70. This forms a larger contact prevention space. The counter side reinforcement portion 232 has a length from the coupling portion base portion 221 to a portion adjacent to the projecting side coupling member 80. This forms a larger contact prevention space. Thus, the counter side reinforcement portion 232 reciprocating in the movable direction DX is less likely to come into contact with the counter movable block 70 and the counter movable coupling portion 130.

The structure of the inner structure protecting portion 240 will now be described.

The inner structure protecting portion 240 will be described with reference to FIGS. 17 to 19. The inner structure protecting portion 240 prevents an inner structure of the electric linear actuator 40 from being damaged due to force acting on the output shaft 20. The inner structure protecting portion 240 cooperates with a main body side protection portion 32 of the main body casing 30 to receive the force applied to the output shaft 20 and thus prevents the inner structure from being damaged. The inner structure of the electric linear actuator 40 includes the block coupling member 100, a member formed integrally with the block coupling member 100, and a member coupled to the block coupling member 100 in the block coupling member 100.

For example, the inner structure protecting portion 240 is integrated with the output functional member 200. The inner structure protecting portion 240 includes a pushing movement restriction portion 241, a pulling movement restriction portion 242, a first rotation restriction portion 243, and a second rotation restriction portion 244.

The main body side protection portion 32 forms part of the main body casing 30. The main body side protection portion 32 and the casing outer wall portion 31 are formed integrally from the same material. The main body side protection portion 32 includes a main body side pushing restriction portion 33, a main body side pulling restriction portion 34, and a main body side rotation restriction portion 35. The main body side rotation restriction portion 35 includes a main body side first restriction portion 35A and a main body side second restriction portion 35B (see FIG. 18).

Figure 17:
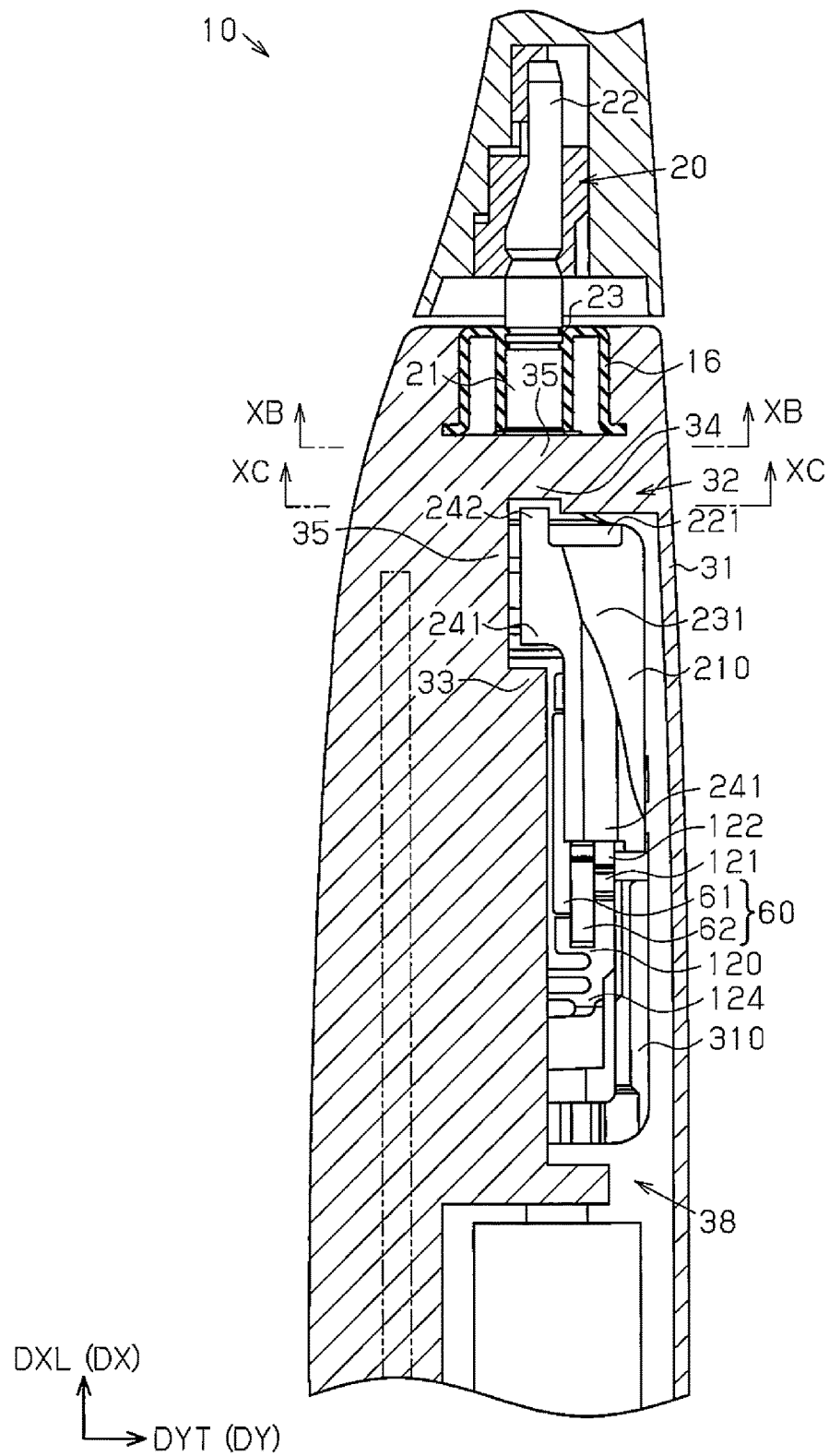
FIG. 17 is a partial cross-sectional view of the electric linear actuator in the first embodiment taken at a different position in the longitudinal direction.

For example, the pushing movement restriction portion 241 has a structure illustrated in FIG. 17. The pushing movement restriction portion 241 is continuous with an end portion of the output side reinforcement portion 231 on the side of the bottom surface direction DYB. The pushing movement restriction portion 241 is coupled to the output side reinforcement portion 231. The pushing movement restriction portion 241 is arranged at a portion further in the projecting direction DXL than the main body side pushing restriction portion 33 in the movable direction DX. The pushing movement restriction portion 241 faces the main body side pushing restriction portion 33 in the movable direction DX. A gap is formed between the pushing movement restriction portion 241 and the main body side pushing restriction portion 33.

When a load for moving the output shaft 20 to the side of the retracting direction DXR is applied to the output shaft 20, the pushing movement restriction portion 241 comes into contact with the main body side pushing restriction portion 33 and thus receives the load applied to the output shaft 20. In other words, the pushing movement restriction portion 241 comes into contact with the main body casing 30 (main body side pushing restriction portion 33, herein), and thus receives the load in a pushing direction from the output shaft 20 to the block coupling member 100. Thus, the inner structure of the electric linear actuator 40 is prevented from being damaged due to the load in the retracting direction DXR (pushing direction) applied to the output shaft 20. The size of the gap between the pushing movement restriction portion 241 and the main body side pushing restriction portion 33 is set to be in such a range that the pushing movement restriction portion 241 and the main body side pushing restriction portion 33 come into contact with each other before the inner structure is damaged due to the load in the retracting direction DXR.

For example, the pulling movement restriction portion 242 has a structure illustrated in FIG. 17. The pulling movement restriction portion 242 is continuous with an end portion of the output side reinforcement portion 231 on the side of the bottom surface direction DYB. The pulling movement restriction portion 242 is coupled to the output side reinforcement portion 231. The pulling movement restriction portion 242 is arranged at a portion further in the retracting direction DXR than the main body side pulling restriction portion 34 in the movable direction DX. The pulling movement restriction portion 242 faces the pulling movement restriction portion 242 in the movable direction DX. A gap is formed between the pulling movement restriction portion 242 and the main body side pulling restriction portion 34.

When a load for moving the output shaft 20 in the projecting direction DXL is applied to the output shaft 20, the pulling movement restriction portion 242 comes into contact with the main body side pulling restriction portion 34 and thus receives the load applied to the output shaft 20. In other words, the pulling movement restriction portion 242 comes into contact with the main body casing 30 (main body side pulling restriction portion 34, herein) to receive a load in a pulling out direction from the block coupling member 100 to the output shaft 20. Thus, the inner structure of the electric linear actuator 40 can be prevented from being damaged due to the load in the projecting direction DXL (pulling out direction) applied to the output shaft 20. The size of the gap between the pulling movement restriction portion 242 and the main body side pulling restriction portion 34 is set to be in such a range that the pulling movement restriction portion 242 and the main body side pulling restriction portion 34 come into contact with each other before the inner structure is damaged due to the load in the projecting direction DXL.

Figure 18:
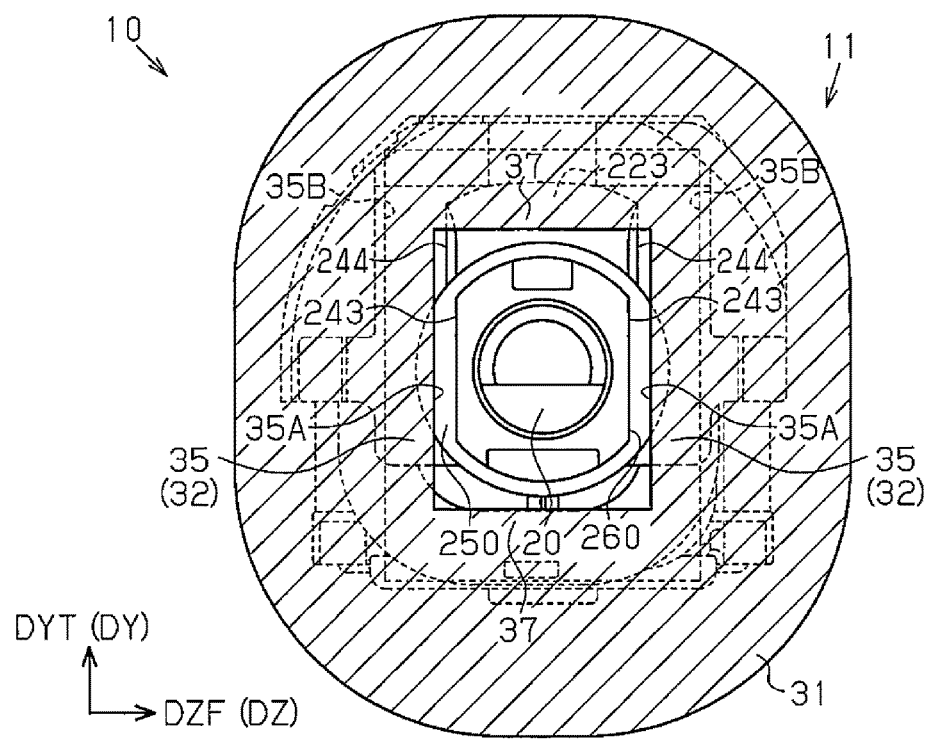
FIG. 18 is a cross-sectional view of the electric linear actuator in the first embodiment taken along line XB-XB in FIG. 17.
Figure 19:
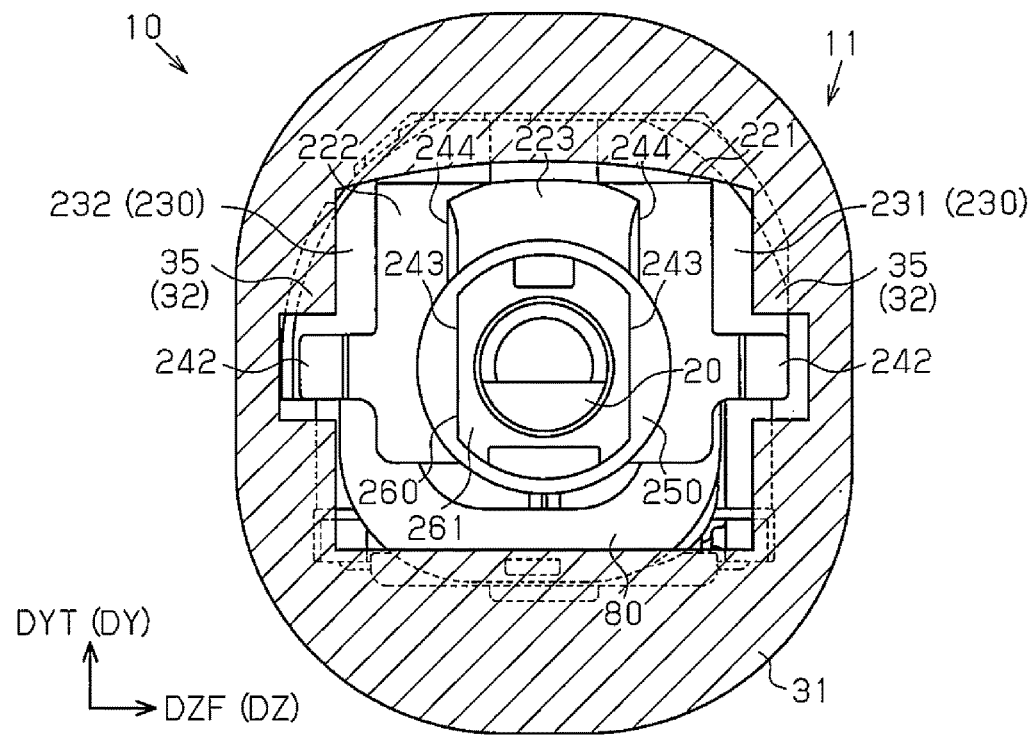
FIG. 19 is a cross-sectional view of the electric linear actuator in the first embodiment taken along line XC-XC in FIG. 17.

For example, the first rotation restriction portion 243 has a structure illustrated in FIG. 18. The first rotation restriction portion 243 is formed at an outer circumferential portion of the member receiving portion 260. An outer surface of the first rotation restriction portion 243 has a flat surface shape. The first rotation restriction portion 243 faces the main body side first restriction portion 35A in the planer direction. A gap is formed between the first rotation restriction portion 243 and the main body side first restriction portion 35A.

When force for rotating the output shaft 20 about the center line is applied to the output shaft 20, the first rotation restriction portion 243 comes into contact with the main body side first restriction portion 35A and thus receives the rotating force applied to the output shaft 20. Thus, the inner structure of the electric linear actuator 40 is prevented from being damaged due to the rotating force applied to the output shaft 20. The size of the gap between the first rotation restriction portion 243 and the main body side first restriction portion 35A is set to be in such a range that the first rotation restriction portion 243 and the main body side first restriction portion 35A come into contact with each other before the inner structure is damaged due to the rotating force on the output shaft 20.

For example, the second rotation restriction portion 244 has a structure illustrated in FIG. 18. The second rotation restriction portion 244 is formed at an outer circumferential portion of the coupling portion outer wall portion 223. An outer surface of the second rotation restriction portion 244 has a flat surface shape. The second rotation restriction portion 244 faces the main body side second restriction portion 35B in the planer direction. A gap is formed between the second rotation restriction portion 244 and the main body side second restriction portion 35B.

When force for rotating the output shaft 20 about the center line is applied to the output shaft 20, the second rotation restriction portion 244 comes into contact with the main body side second restriction portion 35B to receive the rotating force applied to the output shaft 20. Thus, the inner structure of the electric linear actuator 40 is prevented from being damaged due to the rotating force applied to the output shaft 20. The size of the gap between the second rotation restriction portion 244 and the main body side second restriction portion 35B is set to be in such a range that the second rotation restriction portion 244 and the main body side second restriction portion 35B come into contact with each other before the inner structure is damaged due to the rotating force on the output shaft 20. For example, the gap between the second rotation restriction portion 244 and the main body side second restriction portion 35B has a size corresponding to the gap between the first rotation restriction portion 243 and the main body side first restriction portion 35A. With the corresponding gaps, a rotation amount for the first rotation restriction portion 243 and the main body side first restriction portion 35A to come into contact with each other becomes substantially equal to a rotation amount for the second rotation restriction portion 244 and the main body side second restriction portion 35B to come into contact with each other.

The pulling movement restriction portion 242 also functions as a rotation restriction portion for receiving the rotating force on the output shaft 20. For example, the pulling movement restriction portion 242 has a structure illustrated in FIG. 19. An outer surface of the pulling movement restriction portion 242 has a flat surface shape. The pulling movement restriction portion 242 faces the main body side rotation restriction portion 35 in the planer direction. A gap is formed between the pulling movement restriction portion 242 and the main body side rotation restriction portion 35.

When force for rotating the output shaft 20 about the center line is applied to the output shaft 20, the pulling movement restriction portion 242 comes into contact with the main body side rotation restriction portion 35 to receive the rotating force applied to the output shaft 20. Thus, the inner structure of the electric linear actuator 40 is prevented from being damaged due to the rotating force applied to the output shaft 20. The size of the gap between the pulling movement restriction portion 242 and the main body side rotation restriction portion 35 is set to be in such a range that the pulling movement restriction portion 242 and the main body side rotation restriction portion 35 come into contact with each other before the inner structure is damaged due to the rotating force on the output shaft 20. For example, the gap between the pulling movement restriction portion 242 and the main body side rotation restriction portion 35 has a size corresponding to the gap between the first rotation restriction portion 243 and the main body side first restriction portion 35A. With the corresponding gaps, a rotation amount for the first rotation restriction portion 243 and the main body side first restriction portion 35A to come into contact with each other becomes substantially equal to a rotation amount for the pulling movement restriction portion 242 and the main body side rotation restriction portion 35 to come into contact with each other.

The structure of the load receiving portion 250 will now be described.

The load receiving portion 250 will be described with reference to FIGS. 4 to 6, and 16. The load receiving portion 250 has an annular shape. An outer circumference surface of the load receiving portion 250 has a curved surface similar to a spherical surface. The curved surface similar to a spherical surface is similar to an outer circumference surface formed by a single round of a slip portion including the largest diameter portion of a sphere. The load receiving portion 250 is coupled to the coupling portion outer wall portion 223. The load receiving portion 250 is formed on an outer circumference of the coupling portion outer wall portion 223. The load receiving portion 250 projects in the planer direction from the coupling portion outer wall portion 223. The load receiving portion 250 has a structure of receiving a load applied to the output shaft 20. When a load that inclines the output shaft 20 relative to the center line of the main body casing 30 is applied, the load receiving portion 250 comes into contact with a casing load receiving portion 37 of the main body casing 30 to receive the load. The load receiving portion 250 has the curved surface similar to a sphere. Thus, an uneven pressure pattern is less likely to be formed on the casing load receiving portion 37.

The structure of the member receiving portion 260 will now be described.

The member receiving portion 260 will be described with reference to FIGS. 4 to 6, and 16. The member receiving portion 260 has a shape similar to an annular shape. The member receiving portion 260 is coupled to the coupling portion outer wall portion 223. The member receiving portion 260 is formed on an outer circumference of the coupling portion outer wall portion 223. The member receiving portion 260 projects in the planer direction from the coupling portion outer wall portion 223. The member receiving portion 260 is formed at a portion further in the projecting direction DXL than the load receiving portion 250 in the movable direction DX. The member receiving portion 260 is formed at an end portion of the electric linear actuator 40 on the side of the projecting direction DXL in the movable direction DX. The member receiving portion 260 includes a member receiving surface 261. The member receiving portion 260 has a structure for supporting the elastic member 16 of the electric device main body 11 with the member receiving surface 261.

The elastic member 16 is formed from an elastic material. The elastic member 16 has a shape similar to a cylindrical shape. The elastic member 16 is fitted in the fitting groove 23 of the output shaft 20. The elastic member 16 has a structure for sealing a portion between an opening portion of the main body casing 30 and the output shaft 20.

The member receiving surface 261 has a flat surface shape. The member receiving surface 261 is parallel to the planer direction. The member receiving surface 261 forms a surface of a portion of the member receiving portion 260 on the side of the projecting direction DXL. The member receiving surface 261 is in contact with the elastic member 16. The member receiving surface 261 supports the elastic member 16 from the side of the retracting direction DXR. Thus, the movement of the elastic member 16 in the retracting direction DXR relative to the output shaft 20 is restricted.

The member receiving portion 260 has the following advantage. The member receiving portion 260 supports the elastic member 16. Thus, a sealing property of the main body casing 30 can be prevented from deteriorating due to displacement of the elastic member 16 relative to the output shaft 20. The member receiving portion 260 has an advantage over a structure of a comparative example for supporting the elastic member 16.

In the structure of the comparative example, the elastic member 16 is supported by a retaining ring. In the structure of the comparative example, the output shaft 20 includes a retaining ring fitting groove in which the retaining ring is fitted. The retaining ring fitting groove is arranged further in the retracting direction DXR than the fitting groove 23. The retaining ring is fitted in the retaining ring fitting groove. The retaining ring supports the elastic member 16 from the side of the retracting direction DXR. The structure of the comparative example requires the retaining ring and the retaining ring fitting groove.

With the member receiving portion 260, the retaining ring and the retaining ring fitting groove can be omitted. The output shaft vibration-type electric device 10 includes the member receiving portion 260, and thus the retaining ring and the retaining ring fitting groove are omitted. Thus, the number of processes on the output shaft 20 is reduced. Furthermore, a step of fitting the retaining ring in the retaining ring fitting groove is eliminated. Thus, the member receiving portion 260 improves the manufacturing efficiency of the output shaft vibration-type electric device 10.

The structure of the counter functional member 300 will now be described.

The counter functional member 300 will be described with reference to FIGS. 3, 4, 6, 7, and 9. The counter functional member 300 is arranged at a portion further in the retracting direction DXR than the output functional member 200 in the movable direction DX. The counter functional member 300 is arranged at a portion on the side of the top surface direction DYT of the block coupling member 100 in the height direction DY. The counter functional member 300 is arranged from a portion on the side of the front surface direction DZF of the block coupling member 100 to a portion on the side of the rear surface direction DZR of the block coupling member 100 in the width direction DZ.

The counter functional member 300 is formed from a metal material. The counter functional member 300 is long in the movable direction DX. The counter functional member 300 is short in the width direction DZ. The counter functional member 300 is coupled to the counter movable coupling portion 130 with the plurality of fastening members 41. The counter functional member 300 and the counter movable coupling portion 130 are integrated. The counter functional member 300 has a plurality of components, made of the same metal material, formed integrally. The plurality of components of the counter functional member 300 include a counter member main body portion 310 and a counter member adjusting portion 320. The counter functional member 300 is divided into the counter member main body portion 310 and the counter member adjusting portion 320. For example, the counter functional member 300 is formed by bending a plate material. Preferably, the counter functional member 300 cooperates with the additional adjustment member 400 to form a vibration reducing structure.

The counter member main body portion 310 has a flat plate shape. The counter member main body portion 310 is arranged on the top surfaces of the output movable coupling portion 120 and the counter movable coupling portion 130. The output member main body portion 210 is coupled to the counter movable coupling portion 130 with the plurality of fastening members 41. The counter member main body portion 310 forms a base portion of the counter functional member 300.

The counter member adjusting portion 320 has a flat plate shape. The counter member adjusting portion 320 is arranged at a portion further in the retracting direction DXR than the retracting side coupling member 90 in the movable direction DX. Thus, the counter member adjusting portion 320 is arranged further in the retracting direction DXR than the counter movable block 70. The counter member adjusting portion 320 faces the retracting side coupling member 90 in the movable direction DX with a gap in between. The counter member adjusting portion 320 is coupled to the additional adjustment member 400. The counter member adjusting portion 320 includes a structure for balancing the weight of the functional coupled portion including the output movable block 60 and the weight of the functional coupled portion including the counter movable block 70.

The structure of the additional adjustment member 400 will now be described.

Figure 15:
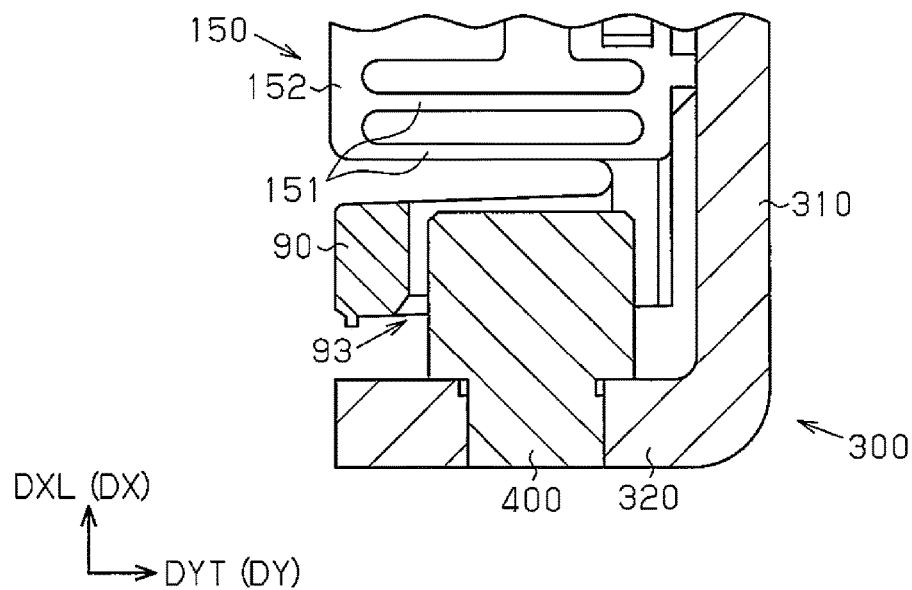
FIG. 15 is a partial cross-sectional view of the electric linear actuator in the first embodiment.

The additional adjustment member 400 will be described with reference to FIGS. 3 and 15. The additional adjustment member 400 is formed from a metal material. The additional adjustment member 400 has a cylindrical shape. Preferably, the additional adjustment member 400 is formed independently from the counter functional member 300. The additional adjustment member 400 is coupled to the counter member adjusting portion 320 with an adhesive. The additional adjustment member 400 is arranged at a portion further in the projecting direction DXL than the counter member adjusting portion 320 in the movable direction DX. The additional adjustment member 400 is partially arranged in the coupling member space 93. The additional adjustment member 400 includes a structure for balancing the weight of the functional coupled portion including the output movable block 60 and the weight of the functional coupled portion including the counter movable block 70.

The vibration reducing structure will now be described.

The vibration reducing structure will be described with reference to FIGS. 3 to 7. The vibration reducing structure includes a first vibration reducing structure and a second vibration reducing structure. When there is no vibration reducing structure, unwanted vibration may occur in the electric linear actuator 40 due to the reasons described below.

The output movable block 60 is coupled to the output functional member 200. The output functional member 200 is coupled to the output shaft 20. Thus, the output movable block 60 receives loads from the output functional member 200 and from the output shaft 20. The first vibration reducing structure balances the loads applied to output movable block 60 and to the counter movable block 70. In other words, when there is no first vibration reducing structure, an unbalanced load may be applied to the output movable block 60 and the counter movable block 70. When the unbalanced load is applied to the output movable block 60 and the counter movable block 70, unwanted vibration resulting from inertial force of the output movable block 60 may be produced in the electric linear actuator 40.

In this example, the first vibration reducing structure balances the load applied to the functional coupled portion including the output movable block 60 and the load applied to the functional coupled portion including the counter movable block 70. Thus, unwanted vibration is prevented in the electric linear actuator 40. For example, the first vibration reducing structure includes the counter functional member 300 and the additional adjustment member 400.

The first vibration reducing structure couples the counter functional member 300 to the counter movable block 70 and balances the load applied to the functional coupled portion including the output movable block 60 and the load weight applied to the functional coupled portion including the counter movable block 70. In this example, the first vibration reducing structure balances the weight applied to the functional coupled portion including the output movable block 60 and the weight applied to the functional coupled portion including the counter movable block 70. This balances the load applied to the two functional coupled portions. The first vibration reducing structure relies mainly on the counter member adjusting portion 320 and the additional adjustment member 400 to resolve the weight unbalance caused by the weight of the output shaft 20.

The output movable block 60, the output movable coupling portion 120, the output functional member 200, and the output shaft 20 form a single functional coupled portion. The counter movable block 70, the counter movable coupling portion 130, the counter functional member 300, and the additional adjustment member 400 form a single functional coupled portion.

The loads applied to the functional coupled portion including the output movable block 60 and the functional coupled portion including the counter movable block 70 are balanced with the first vibration reducing structure. Thus, unwanted vibration is less likely to occur in the electric linear actuator 40 when the output movable block 60 and the counter movable block 70 reciprocate.

The electric linear actuator 40 may produce moment (hereinafter, referred to as "output side moment") through reciprocation of the output movable block 60. The output side moment affects the magnitude of the unwanted vibration. The electric linear actuator 40 may produce moment (hereinafter, referred to as "counter side moment") through reciprocation of the counter movable block 70. The counter side moment affects the magnitude of the unwanted vibration. The second vibration reducing structure prevents the unwanted vibration that may occur due to the output side moment and the counter side moment. In other words, when there is no second vibration reducing structure, the unwanted vibration may occur in the electric linear actuator 40 due to the output side moment and the counter side moment.

The second vibration reducing structure decrease the distance between the center of gravity of the functional coupled portion including the output movable block 60 and the center of gravity of the functional coupled portion including the counter movable block 70. Thus, the vibration caused by moment is less likely to occur. In this example, the second vibration reducing structure increases the total weight of the counter member adjusting portion 320 and the additional adjustment member 400 to be greater than the weight of the counter member main body portion 310. This offsets the above distance. In other words, the second vibration reducing structure increases the offsetting of the output side moment and the counter side moment. Thus, unwanted vibration is less likely to occur in the electric linear actuator 40 when the output movable block 60 and the counter movable block 70 reciprocate.

For example, the centers of gravity of the functional coupled portions have the following relationship.

The electric linear actuator 40 includes a first section and a second section in a front view (see FIG. 5) and a rear view (see FIG. 6) of the electric linear actuator 40. The first section and the second section are separated along a coupling portion center line of the output shaft coupling portion 220 extending in the axial direction of the output shaft 20. In FIG. 6, the first section is arranged further in the top surface direction DYT than the coupling portion center line in the height direction DY. The second section is arranged further in the bottom surface direction DYB than the coupling portion center line in the height direction DY.

The first section at least includes the counter movable block 70. In this example, the output movable block 60 and the counter movable block 70 are arranged in the first center section. Preferably, the center of gravity of the functional coupled portion including the output movable block 60 and the center of gravity of the functional coupled portion including the counter movable block 70 are located in the first section. Thus, the centers of gravity of the functional coupled portions are preferably arranged close to each other in the first section.

A fixing structure of the electric linear actuator 40 will now be described.

The fixing structure will be described with reference to FIG. 16. The main body casing 30 includes a plurality of casing side coupling portions 36 and a plurality of fastening members 17. An outer surface of the casing side coupling portion 36 has a flat surface shape. The outer surface of the casing side coupling portion 36 has a shape that is parallel to the coupling portion supporting surface 111 (see FIG. 4) of the fixing coupling portion 110. The outer surface of the casing side coupling portion 36 is in contact with the coupling portion supporting surface 111.

The fixing coupling portion 110 on the side of the projecting direction DXL is coupled to one of the casing side coupling portions 36 by the fastening member 17. The fixing coupling portion 110 on the side of the projecting direction DXL is coupled to the other casing side coupling portions 36 by the fastening member 17. The fixing coupling portion 110 and the casing side coupling portion 36 are integrated. The fixing coupling portion 110 and the fixed block 50 are integrated. Thus, the fixed block 50, the fixing coupling portion 110, and the casing side coupling portion 36 are integrated.

The fixing coupling portion 110 and the casing side coupling portion 36 prevent the electric linear actuator 40 from being separated from the main body casing 30 when the load is applied to the output shaft 20. For example, the output shaft 20 receives a load including a component in the planar direction. The load received by the output shaft 20 is transmitted to the components of the electric linear actuator 40. The load received by the components of the electric linear actuator 40 causes the electric linear actuator 40 to incline relative to the center line of the main body casing 30. The fixing coupling portion 110 and the casing side coupling portion 36 are coupled to each other in such a manner as to receive the load applied to the components of the electric linear actuator 40. This limits inclination of the electric linear actuator 40 relative to the main body casing 30. Thus, the fixing coupling portion 110 and the casing side coupling portion 36 are coupled to each other to improve the rigidity of the electric linear actuator 40 against the load applied to the output shaft 20.

The operation of the electric linear actuator 40 will now be described.

The operation will be described with reference to FIGS. 1 to 3. When current is supplied to the coil 52 from the controller 14, the fixed block 50 forms a magnetic field. The output movable block 60 is reciprocated in the movable direction DX by the electromagnetic force acting between the output movable block 60 and the fixed block 50. The counter movable block 70 is reciprocated in the movable direction DX by the electromagnetic force acting between counter movable block 70 and the fixed block 50. The output movable block 60 and the counter movable block 70 reciprocate in opposite phases. The output functional member 200 and the output movable block 60 reciprocate integrally. The output shaft 20 and the output functional member 200 reciprocate integrally. As described above, the electric linear actuator 40 reciprocates the output movable block 60. This reciprocates the output shaft 20.

The electric linear actuator 40 has the advantages described below.

(1) The electric linear actuator 40 includes the projecting side coupling member 80 and the retracting side coupling member 90. The projecting side coupling member 80 and the retracting side coupling member 90 have different shapes. This increases the degree of freedom for the structures of the coupling members 80 and 90. Thus, favorable resonant driving may be achieved, while avoiding enlargement of the electric linear actuator 40 that would be caused by the structures of the coupling members 80 and 90.

(2) The projecting side coupling member 80 is thinner than the retracting side coupling member 90. Thus, the projecting side coupling member 80 is less likely to come into contact with the output functional member 200. This limits damage to the projecting side coupling member 80.

(3) The projecting side coupling member 80 has an asymmetric shape with respect to the center line in the width direction DZ in a side view of the electric linear actuator 40 on the side of the projecting direction DXL.

This increases the degree of freedom for the structure of the coupling member 80. Thus, favorable rigidity of the projecting side coupling member 80 may be achieved, while avoiding enlargement of the electric linear actuator 40 that would be caused by the structure of the coupling member 80.

(4) The electric linear actuator 40 includes the counter functional member 300. This balances the loads applied to the output movable block 60 and the counter movable block 70. Thus, unwanted vibration in the electric linear actuator 40 can be limited.

(5) The electric linear actuator 40 includes the block coupling member 100. The block coupling member 100 has a structure in which a plurality of components are formed integrally from a resin material. The projecting side coupling member 80 and the retracting side coupling member 90 are formed integrally with the block coupling member 100 from a resin material. This increases the productivity of the block coupling member 100, the projecting side coupling member 80, and the retracting side coupling member 90.

(6) The block coupling member 100 includes the coupling portion supporting surface 111. The coupling portion supporting surface 111 is coupled to the casing side coupling portion 36 of the main body casing 30. The coupling portion supporting surface 111 cooperates with the casing side coupling portion 36 to receive the load on the output shaft 20. In this structure, the external load acting on the output shaft 20 is received by the coupling portion supporting surface 111 and the casing side coupling portion 36. This restricts inclination of the electric linear actuator 40 relative to the center line of the main body casing 30 that would be caused by the load applied to the output shaft 20.

(7) The output functional member 200 includes the output shaft coupling portion 220. Thus, the output shaft 20 is coupled to the output shaft coupling portion 220. This appropriately holds the output shaft 20.

(8) The output shaft coupling portion 220 includes the coupling portion outer wall portion 223. The coupling portion outer wall portion 223 supports the outer circumferential portion of the output shaft 20. This structure increases the area of the portion holding the output shaft 20. This further increases the effect for appropriately holding the output shaft 20.

(9) The coupling portion outer wall portion 223 projects toward the side of the projecting direction DXL from the coupling portion base surface 222. This structure increases the adjusted width in the length of the coupling portion outer wall portion 223 in the movable direction DX. Thus, the effect for appropriately holding the output shaft 20 is further increased.

(10) The output functional member 200 includes the load receiving portion 250. Thus, the load receiving portion 250 and the casing load receiving portion 37 can receive the external load acting on the output shaft 20. This restricts inclination of the electric linear actuator 40 relative to the center line of the main body casing 30 that would be caused by the load applied to the output shaft 20.

(11) The load receiving portion 250 has a curved surface similar to a spherical surface. Thus, an uneven pressure pattern is less likely to be formed on the casing load receiving portion 37 by the load receiving portion 250. Thus, the load applied to the output shaft 20 is further stably received by the load receiving portion 250.

(12) The output functional member 200 includes the member receiving portion 260. This structure restricts movement of the elastic member 16 of the electric device main body 11 relative to the output shaft 20. Thus, deterioration of the sealing property that would be caused by the elastic member 16 is limited.

(13) The output functional member 200 includes the output member reinforcement portion 230. The output member reinforcement portion 230 reinforces the output member main body portion 210 and the output shaft coupling portion 220. This limits damage to the output functional member 200 that would be caused by the load applied to the output shaft 20.

(14) The output functional member 200 includes the output side reinforcement portion 231 as the output member reinforcement portion 230. The output side reinforcement portion 231 is adjacent to the output movable block 60. The output side reinforcement portion 231 integrally moves with the output movable block 60. Thus, the output side reinforcement portion 231 is less likely to come into contact with the output movable block 60. This allows for enlargement of the output side reinforcement portion 231. Thus, the output side reinforcement portion 231 increases the rigidity of the output functional member 200.

(15) The output functional member 200 includes the counter side reinforcement portion 232 as the output member reinforcement portion 230. The counter side reinforcement portion 232 is adjacent to the counter movable block 70. Thus, a higher rigidity of the output functional member 200 can be achieved.

(16) The output functional member 200 includes the pushing movement restriction portion 241 as the inner structure protecting portion 240. The pushing movement restriction portion 241 comes into contact with the main body side pushing restriction portion 33 of the main body casing 30 to receive the load in the pushing direction acting on the block coupling member 100 from the output shaft 20. This limits damage to the inner structure of the electric linear actuator 40 that would be caused by the load applied to the output shaft 20.

(17) The output functional member 200 includes the pulling movement restriction portion 242 as the inner structure protecting portion 240. The pulling movement restriction portion 242 comes into contact with the main body side pulling restriction portion 34 of the main body casing 30 to receive the load in the pulling out direction from the block coupling member 100 to the output shaft 20. This limits damage to the inner structure of the electric linear actuator 40 that would be caused by the load applied to the output shaft 20.

(18) The output functional member 200 includes the first rotation restriction portion 243 as the inner structure protecting portion 240. The first rotation restriction portion 243 comes into contact with the main body side first restriction portion 35A of the main body casing 30 to receive the rotating force acting on the output shaft 20. This limits damage of the inner structure of the electric linear actuator 40 that would be caused by the rotating force applied to the output shaft 20.

(19) The counter functional member 300 includes the counter member main body portion 310 and the counter member adjusting portion 320. The counter member main body portion 310 and the counter member adjusting portion 320 are formed integrally from the same material. This reduces the number of manufacturing steps compared to when the counter member main body portion 310 and the counter member adjusting portion 320 are independently formed.

(20) The electric linear actuator 40 includes the additional adjustment member 400. The additional adjustment member 400 is coupled to the counter member adjusting portion 320. This structure allows for adjustment in the position of the center of gravity of the counter movable block 70 by changing the weight of the additional adjustment member 400. Thus, the position of the center of gravity can be adjusted with a higher degree of freedom.

(21) The additional adjustment member 400 is arranged at a portion further in the counter movable block 70 than the counter member adjusting portion 320 in the movable direction DX. This structure reduces the size of the electric linear actuator 40 in the longitudinal direction compared with when the additional adjustment member 400 is arranged closer to the retracting direction DXR than the counter member adjusting portion 320.

(22) The weight of the additional adjustment member 400 is greater than the weight of the counter member main body portion 310. This shortens the distance between the center of gravity of the functional coupled portion including the output movable block 60 and the center of gravity of the functional coupled including the counter movable block 70 can be achieved. Thus, unwanted vibration is limited in the electric linear actuator 40.

Second Embodiment

Figure 14:
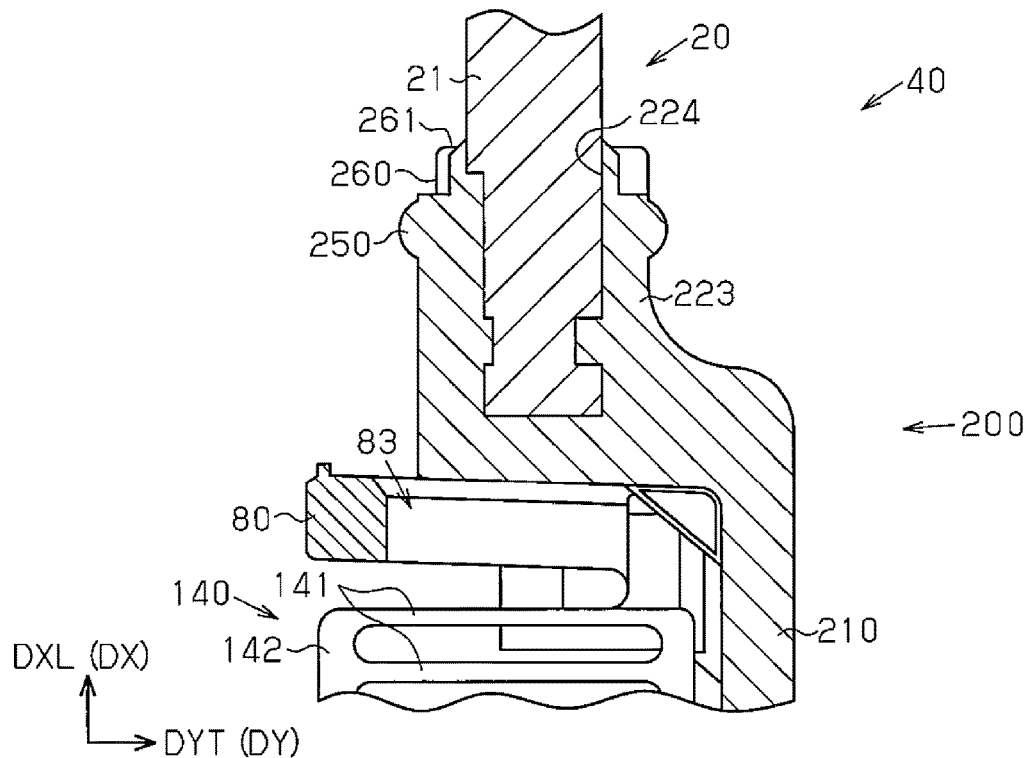
FIG. 14 is a partial cross-sectional view of the electric linear actuator in the first embodiment.

An electric linear actuator 40 of a second embodiment differs from the electric linear actuator 40 of the first embodiment in the points described below but otherwise has the same structure. The electric linear actuator 40 of the first embodiment has the structure illustrated in FIG. 14. The electric linear actuator 40 of the second embodiment has the structure illustrated in FIG. 20. Same reference numerals are given to those components in the electric linear actuator 40 of the second embodiment that are the same as the corresponding components of the first embodiment. Such components will not be described in detail.

Figure 20:
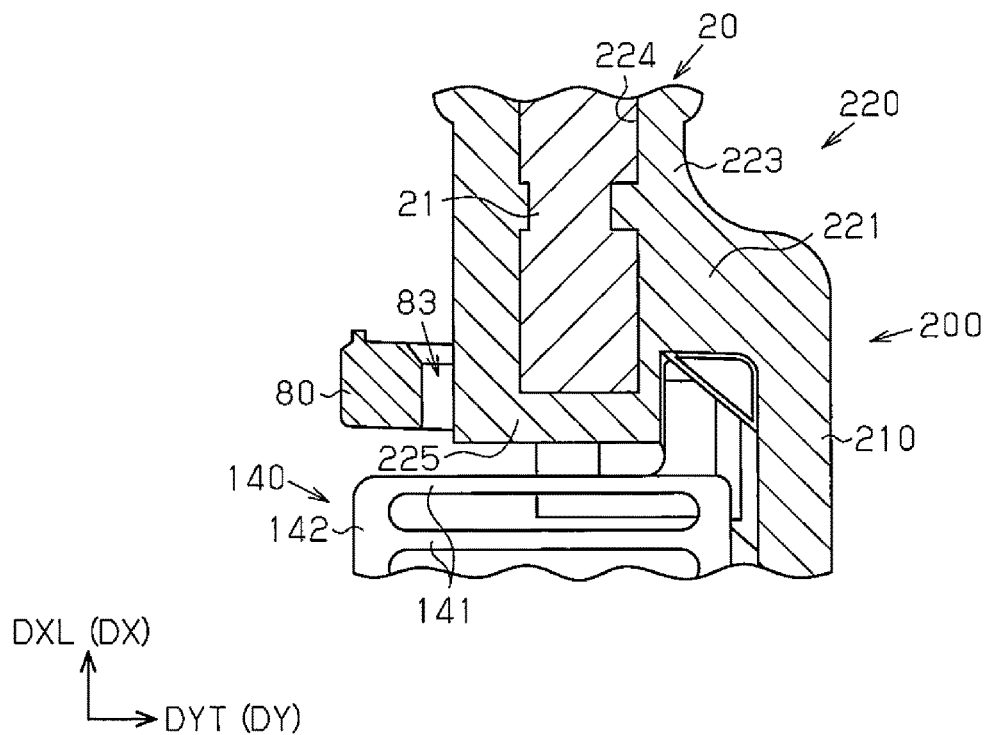
FIG. 20 is a partial cross-sectional view of an electric linear actuator in a second embodiment.

The electric linear actuator 40 of the second embodiment will be described with reference to FIG. 20. The output shaft coupling portion 220 of the electric linear actuator 40 includes a coupling portion extended portion 225.

The coupling portion extended portion 225 has a cylindrical shape. The coupling portion extended portion 225 is continuous with the coupling portion base portion 221. The coupling portion extended portion 225 projects in the retracting direction DXR from a surface of the coupling portion base portion 221 opposite to the coupling portion base surface 222. The coupling portion extended portion 225 is positioned in the coupling member space 83 formed on an inner side of the projecting side coupling member 80. Thus, the output shaft coupling portion 220 is partially arranged in the coupling member space 83. The coupling portion extended portion 225 forms part of the coupling portion inner space 224. The coupling portion inner space 224 is arranged over the coupling portion outer wall portion 223, the coupling portion base portion 221, and the coupling portion extended portion 225.

The coupling portion outer wall portion 223, the coupling portion base portion 221, and the coupling portion extended portion 225 accommodate the shaft base portion 21 in the coupling portion inner space 224. The coupling portion outer wall portion 223, the coupling portion base portion 221, and the coupling portion extended portion 225 are coupled to the shaft base portion 21. The coupling portion outer wall portion 223, the coupling portion base portion 221, and the coupling portion extended portion 225 surround the outer circumference of the shaft base portion 21.

The electric linear actuator 40 in the second embodiment has advantages that are the same as advantages (1) to (22) of the electric linear actuator 40 in the first embodiment. Further, the electric linear actuator 40 has the following advantage.

(23) The output functional member 200 includes the coupling portion extended portion 225. This increases the area in the output shaft coupling portion 220 where the output shaft 20 is held. Thus, the effect for appropriately holding the output shaft 20 is further improved.

Third Embodiment

An electric linear actuator 40 of a third embodiment differs from the electric linear actuator 40 of the first embodiment in the points described below but otherwise has the same structure. The electric linear actuator 40 in the first embodiment has the structure illustrated in FIG. 15. The vibration reducing structure in the first embodiment includes the counter member adjusting portion 320 and the additional adjustment member 400. The electric linear actuator 40 in the third embodiment has the structure illustrated in FIG. 21. The vibration reducing structure in the third embodiment does not include the additional adjustment member 400 but includes a first deformation adjusting portion 330. Same reference numerals are given to those components in the electric linear actuator 40 of the third embodiment that are the same as the corresponding components of the first embodiment. Such components will not be described in detail.

Figure 21:
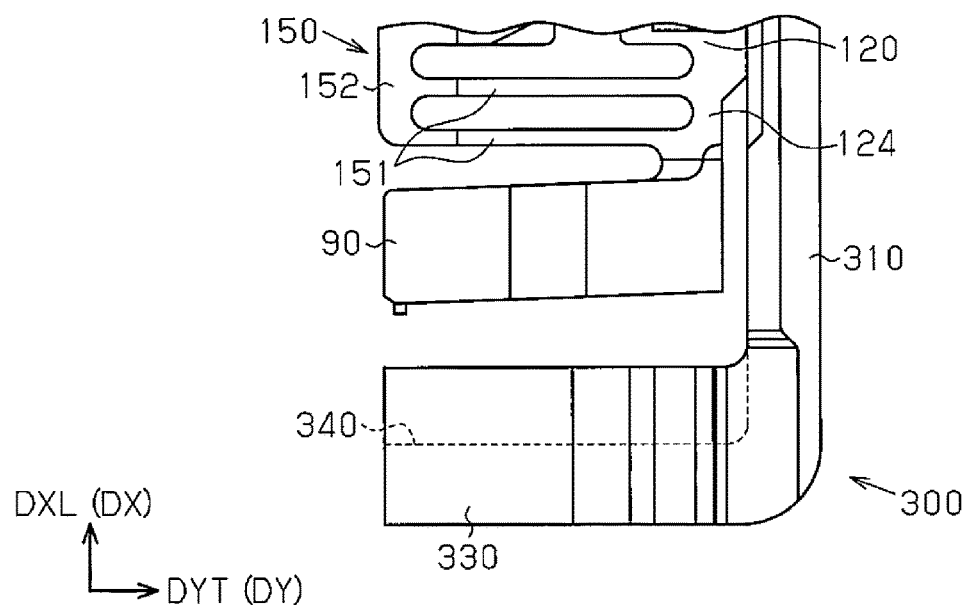
FIG. 21 is a partial front view of an electric linear actuator in a third embodiment.
Figure 22:
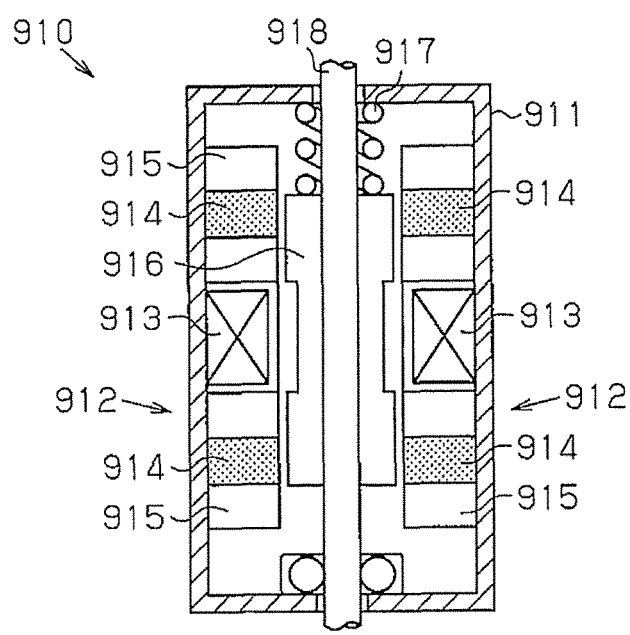
FIG. 22 is a cross-sectional view of a first conventional actuator.
Figure 23:
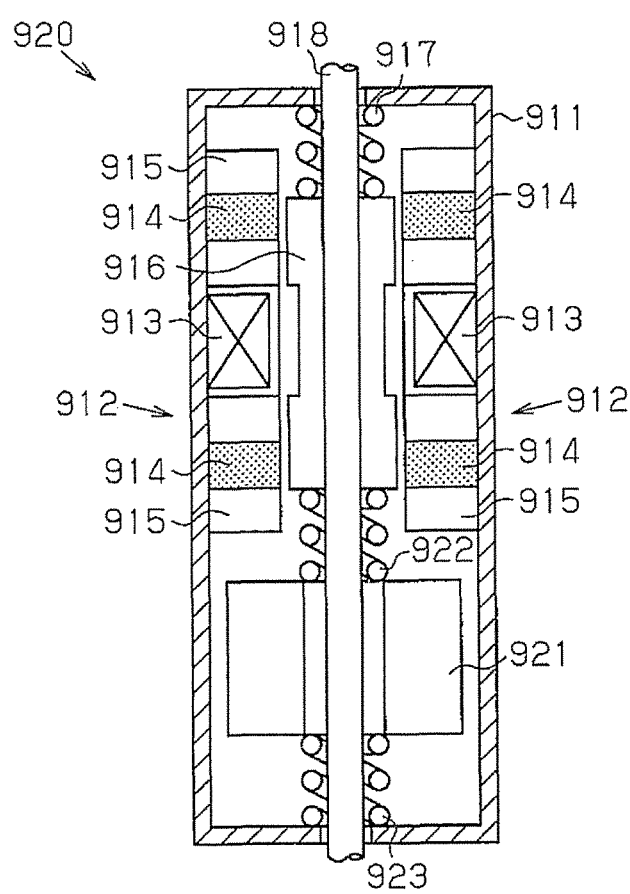
FIG. 23 is a cross-sectional view of a second conventional actuator.
Figure 24:
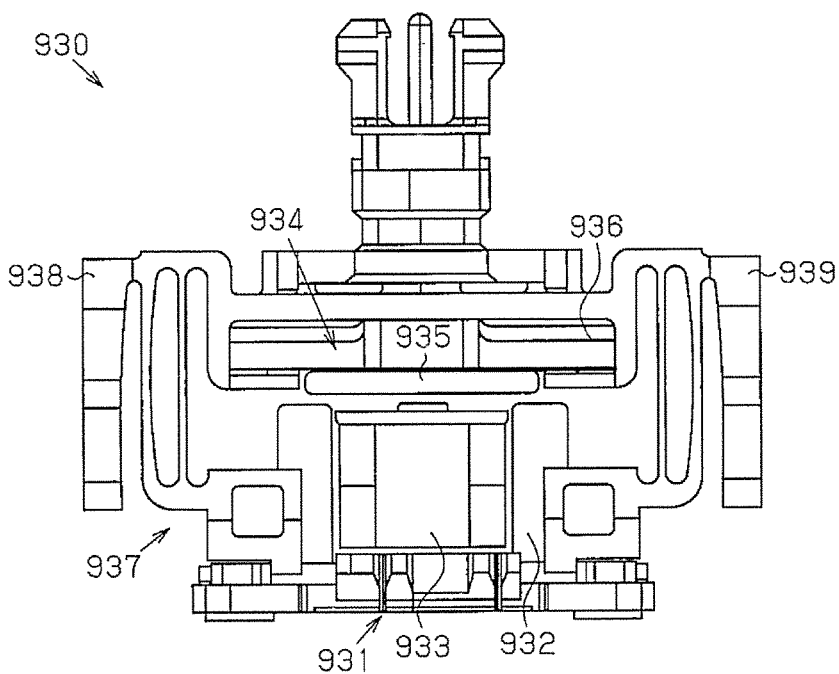
FIG. 24 is a front view of a third conventional actuator.
Figure 25:
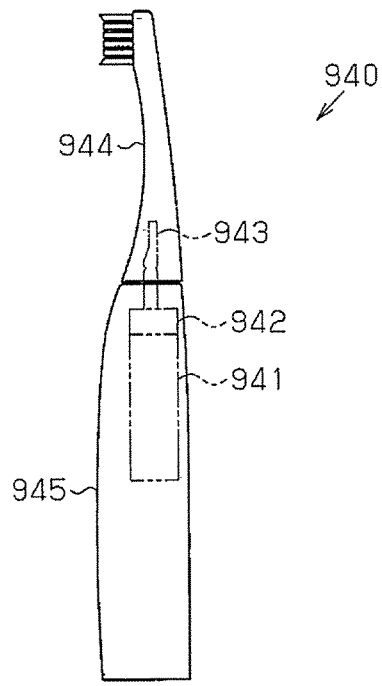
FIG. 25 is a front view of an example of an electric oral hygiene device.

The electric linear actuator 40 in the third embodiment will be described with reference to FIG. 21. In the electric linear actuator 40, the additional adjustment member 400 in the first embodiment is omitted. The counter functional member 300 includes the first deformation adjusting portion 330 instead of the counter member adjusting portion 320. The first deformation adjusting portion 330 also functions as the counter member adjusting portion. The first deformation adjusting portion 330 is thicker than the counter member adjusting portion 320 in the first embodiment. The first deformation adjusting portion 330 is heavier than the counter member main body portion 310. The first deformation adjusting portion 330 is heavier than the counter member adjusting portion 320 in the first embodiment. The weight of the first deformation adjusting portion 330 is the same as the total weight of the weight of the counter member adjusting portion 320 in the first embodiment and the weight of the additional adjustment member 400 in the first embodiment.

The counter functional member 300 in the third embodiment forms a first vibration reducing structure and a second vibration reducing structure similar to the first vibration reducing structure and the second vibration reducing structure in the first embodiment. This indicates that the additional adjustment member 400 is not necessarily required for forming the first vibration reducing structure and the second vibration reducing structure. The first vibration reducing structure can be formed of various structures to balance the weight of the functional coupled portion including the output movable block 60 and the weight of the functional coupled portion including the counter movable block 70. The second vibration reducing structure can be formed of various structures for achieving a short distance between the center of gravity of the functional coupled portion including the output movable block 60 and the center of gravity of the functional coupled portion including the counter movable block 70.

The electric linear actuator 40 of the third embodiment has advantages that are the same as advantages (1) to (22) of the electric linear actuator 40 in the first embodiment. Further, the electric linear actuator 40 of the third embodiment has the following advantage.

(24) In the electric linear actuator 40, the additional adjustment member 400 of the first embodiment is omitted. This reduces the number of manufacturing steps. Thus, the vibration reducing structure may be formed, while improving the manufacturing efficiency.

Fourth Embodiment

An electric linear actuator 40 of a fourth embodiment differs from the electric linear actuator 40 in the following point but otherwise has the same structure. The electric linear actuator 40 in the first embodiment has the structure illustrated in FIG. 15. The electric linear actuator 40 in the first embodiment includes the first vibration reducing structure and the second vibration reducing structure. In contrast, the electric linear actuator 40 of the fourth embodiment has the structure illustrated in FIG. 21. The electric linear actuator 40 of the fourth embodiment includes the first vibration reducing structure and a third vibration reducing structure. Same reference numerals are given to those components in the electric linear actuator 40 of the fourth embodiment that are the same as the corresponding components of the first embodiment. Such components will not be described in detail.

The electric linear actuator 40 of the fourth embodiment will be described with reference to FIG. 21. In the electric linear actuator 40, the additional adjustment member 400 in the first embodiment is plugged. The counter functional member 300 includes a second deformation adjusting portion 340 instead of the counter member adjusting portion 320. The second deformation adjusting portion 340 also functions as the counter member adjusting portion.

The second deformation adjusting portion 340 forms the third vibration reducing structure. The structure of the second deformation adjusting portion 340 corresponds to a structure in which an insertion hole (see FIG. 7) of the counter member adjusting portion 320, to which the additional adjustment member 400 in the first embodiment is coupled, is plugged. The second deformation adjusting portion 340 and the counter member adjusting portion 320 have the same thickness. The second deformation adjusting portion 340 is lighter than the counter member main body portion 310.

The third vibration reducing structure reduces unwanted vibration caused by counter side moment by decreasing the distance between the center of gravity (hereinafter, referred to as counter side center of gravity) of the functional coupled portion including the counter movable block 70 and a center point of the counter side moment. The center point of the counter side moment is within a range including the counter retracting side coupling portion 134 (see FIG. 10). In the third vibration reducing structure, the counter member main body portion 310 is set to be heavier than the second deformation adjusting portion 340 so that the distance is offset to achieve the small counter side moment. Thus, unwanted vibration is less likely to occur in the electric linear actuator 40 when the output movable block 60 and the counter movable block 70 reciprocate.

The counter side center of gravity and the center point of the counter side moment have the following relationship for example.

The counter movable block 70 is arranged in the first section. The center of gravity (counter side center of gravity) of the functional coupled portion including the counter movable block 70 is located in the first section. The arrangement of the counter side center of gravity in the first section decreases the distance between the counter side center of gravity and the center point of the counter side moment.

The electric linear actuator 40 of the fourth embodiment has advantages that are the same as advantages (1) to (21) of the electric linear actuator 40 of the first embodiment. Further, the electric linear actuator 40 of the fourth embodiment has the following advantage.

(25) The counter functional member 300 includes the second deformation adjusting portion 340. The second deformation adjusting portion 340 forms the third vibration reducing structure. The third vibration reducing structure limits unwanted vibration by decreasing the counter side moment during the reciprocation of the electric linear actuator 40.

Other Embodiments

The output shaft vibration-type electric device includes other embodiments that differ from the first embodiment to the fourth embodiment. For example, other embodiments include modifications of the first embodiment to Xth embodiment as described below. The following modifications can be combined as long as there is no technical contradiction.

The electric linear actuator 40 in the first embodiment to the fourth embodiment achieves preferable resonant driving by adjusting the thicknesses of the projecting side coupling member 80 and the retracting side coupling member 90. However, the structure for achieving the preferable resonant driving is not limited to that exemplified in the embodiments. For example, an electric linear actuator in a modification adjusts a path length of the coupling member output side end portion 81 and the coupling member counter side end portion 82 and a path length of the coupling member output side end portion 91 and the coupling member counter side end portion 92. In this modification, the preferable resonant driving is achieved with different path lengths of the projecting side coupling member and the retracting side coupling member. Thus, the preferable resonant driving is achieved with the different shapes of the projecting side coupling member and the retracting side coupling member.

The electric linear actuator 40 in the first embodiment to the fourth embodiment includes the projecting side coupling member 80. However, the structure of the electric linear actuator 40 is not limited to that exemplified in the embodiments. For example, an electric linear actuator 40 in a modification includes a modified projecting side coupling member instead of the projecting side coupling member 80. The modified projecting side coupling member has a function corresponding to the function of the projecting side coupling member 80 but has a structure differing from that of the projecting side coupling member 80.

The electric linear actuator 40 of the first embodiment to the fourth embodiment includes the retracting side coupling member 90. However, the structure of the electric linear actuator 40 is not limited to that exemplified in the embodiments. For example, an electric linear actuator 40 in a modification includes a modified retracting side coupling member instead of the retracting side coupling member 90. The modified retracting side coupling member has a function corresponding to the function of the retracting side coupling member 90 and a structure that differs from that of the retracting side coupling member 90.

In the first embodiment to the fourth embodiment, the projecting side coupling member 80 and the block coupling member 100 are formed integrally from the same resin material. However, the structure of the projecting side coupling member 80 is not limited to that exemplified in the embodiments. For example, a projecting side coupling member 80 in a modification is formed independently from the block coupling member 100 and is coupled to the block coupling member 100. The projecting side coupling member 80 of the modification and the block coupling member 100 are formed from the same material or from different materials.

In the first embodiment to the fourth embodiment, the retracting side coupling member 90 and the block coupling member 100 are formed integrally from the same resin material. However, the structure of the retracting side coupling member 90 is not limited to that exemplified in the embodiments. For example, a retracting side coupling member 90 of a modification is formed independently from the block coupling member 100 and is coupled to the block coupling member 100. The retracting side coupling member 90 of the modification and the block coupling member 100 are formed from the same resin material or from different resin materials.

The block coupling member 100 in the first embodiment to the fourth embodiment includes the fixing coupling portion 110. However, the structure of the block coupling member 100 is not limited to that exemplified in the embodiments. For example, a block coupling member 100 in a modification includes a modified fixing coupling portion instead of the fixing coupling portion 110. The modified fixing coupling portion has a function corresponding to the function of the fixing coupling portion 110 and a structure that differs from that of the fixing coupling portion 110.

The block coupling member 100 in the first embodiment to the fourth embodiment includes the output movable coupling portion 120. However, the structure of the block coupling member 100 is not limited to that exemplified in the embodiments. For example, a block coupling member 100 in a modification includes a modified output movable coupling portion instead of the output movable coupling portion 120. The modified output movable coupling portion has a function corresponding to the function of the output movable coupling portion 120 and a structure that differs from that of the output movable coupling portion 120.

The block coupling member 100 in the first embodiment to the fourth embodiment includes the counter movable coupling portion 130. However, the structure of the block coupling member 100 is not limited to that exemplified in the embodiments. For example, a block coupling member 100 in a modification includes a modified counter movable coupling portion instead of the counter movable coupling portion 130. The modified counter movable coupling portion has a function corresponding to the function of the counter movable coupling portion 130 and a structure that differs from that of the counter movable coupling portion 130.

The block coupling member 100 in the first embodiment to the fourth embodiment includes the projecting side supporting portion 140. However, the structure of the block coupling member 100 is not limited to that exemplified in the embodiments. For example, a block coupling member 100 in a modification includes a modified projecting side supporting portion instead of the projecting side supporting portion 140. The modified projecting side supporting portion has a function corresponding to the function of the projecting side supporting portion 140 and a structure that differs from that of the projecting side supporting portion 140.

The block coupling member 100 in the first embodiment to the fourth embodiment includes the retracting side supporting portion 150. However, the structure of the block coupling member 100 is not limited to that exemplified in the embodiments. For example, a block coupling member 100 in a modification includes a modified retracting side supporting portion instead of the retracting side supporting portion 150. The modified retracting side supporting portion has a function corresponding to the function of the retracting side supporting portion 150 and a structure that differs from that of the retracting side supporting portion 150.

The block coupling member 100 in the first embodiment to the fourth embodiment includes the two output side resin inlet portions 121. However, the structure of the block coupling member 100 is not limited to that exemplified in the embodiments. For example, a block coupling member 100 in a modification has at least one of the two output side resin inlet portions 121 omitted. For example, a block coupling member 100 in another modification includes a modified output side resin inlet portion instead of the output side resin inlet portion 121. The modified output side resin inlet portion has a function corresponding to the function of the output side resin inlet portion 121 and a structure that differs from that of the output side resin inlet portion 121.

The block coupling member 100 in the first embodiment to the fourth embodiment includes the output side resin flow path portion 122. However, the structure of the block coupling member 100 is not limited to that exemplified in the embodiments. A block coupling member 100 in a modification has the output side resin flow path portion 122 omitted. For example, a block coupling member 100 in another modification includes a modified output side resin flow path portion instead of the output side resin flow path portion 122. The modified output side resin flow path portion has a function corresponding to the function of the output side resin flow path portion 122 and a structure that differs from that of the output side resin flow path portion 122.

The block coupling member 100 in the first embodiment to the fourth embodiment includes the output projecting side coupling portion 123. However, the structure of the block coupling member 100 is not limited to that exemplified in the embodiments. A block coupling member 100 in a modification has the output projecting side coupling portion 123 omitted. For example, a block coupling member 100 in another modification includes a modified output projecting side coupling portion instead of the output projecting side coupling portion 123. The modified output projecting side coupling portion has a function corresponding to the function of the output projecting side coupling portion 123 and a structure that differs from that of the output projecting side coupling portion 123.

The block coupling member 100 in the first embodiment to the fourth embodiment includes the output retracting side coupling portion 124. However, the structure of the block coupling member 100 is not limited to that exemplified in the embodiments. A block coupling member 100 in a modification has the output retracting side coupling portion 124 omitted. For example, a block coupling member 100 in another modification includes a modified output retracting side coupling portion instead of the output retracting side coupling portion 124. The modified output retracting side coupling portion has a function corresponding to the function of the output retracting side coupling portion 124 and a structure that differs from that of the output retracting side coupling portion 124.

The block coupling member 100 in the first embodiment to the fourth embodiment includes the two counter side resin inlet portions 131. However, the structure of the block coupling member 100 is not limited to that exemplified in the embodiments. A block coupling member 100 in a modification has at least one of the two counter side resin inlet portions 131 omitted. For example, a block coupling member 100 in another modification includes a modified counter side resin inlet portion instead of the counter side resin inlet portion 131. The modified counter side resin inlet portion has a function corresponding to the function of the counter side resin inlet portion 131 and a structure that differs from that of the counter side resin inlet portion 131.

The block coupling member 100 in the first embodiment to the fourth embodiment includes the counter side resin flow path portion 132. However, the structure of the block coupling member 100 is not limited to that exemplified in the embodiments. A block coupling member 100 in a modification has the counter side resin flow path portion 132 omitted. For example, a block coupling member 100 in another modification includes a modified counter side resin flow path portion instead of the counter side resin flow path portion 132. The modified counter side resin flow path portion has a function corresponding to the function of the counter side resin flow path portion 132 and a structure that differs from that of the counter side resin flow path portion 132.

The block coupling member 100 in the first embodiment to the fourth embodiment includes the counter projecting side coupling portion 133. However, the structure of the block coupling member 100 is not limited to that exemplified in the embodiments. A block coupling member 100 in a modification has the counter projecting side coupling portion 133 omitted. For example, a block coupling member 100 in another modification includes a modified counter projecting side coupling portion instead of the counter projecting side coupling portion 133. The modified counter projecting side coupling portion has a function corresponding to the function of the counter projecting side coupling portion 133 and a structure that differs from that of the counter projecting side coupling portion 133.

The block coupling member 100 in the first embodiment to the fourth embodiment includes the counter retracting side coupling portion 134. However, the structure of the block coupling member 100 is not limited to that exemplified in the embodiments. A block coupling member 100 in a modification has the counter retracting side coupling portion 134 omitted. For example, a block coupling member 100 in another modification includes a modified counter retracting side coupling portion instead of the counter retracting side coupling portion 134. The modified counter retracting side coupling portion has a function corresponding to the function of the counter retracting side coupling portion 134 and a structure that differs from that of the counter retracting side coupling portion 134.

The output functional member 200 in the first embodiment to the fourth embodiment is formed from a resin material. However, the material of the output functional member 200 is not limited to that exemplified in the embodiments. For example, an output functional member 200 in a modification is formed from a metal material.

The output functional member 200 in the first embodiment to the fourth embodiment is coupled to the output movable block 60 by the output movable coupling portion 120. However, how the output functional member 200 is coupled is not limited to that exemplified in the embodiments. For example, an output functional member 200 in a modification is directly coupled to the output movable block 60. The output functional member 200 need only be movably coupled to the output movable block 60.

The output functional member 200 in the first embodiment to the fourth embodiment includes the output member main body portion 210. However, the structure of the output functional member 200 is not limited to that exemplified in the embodiments. For example, an output functional member 200 in a modification includes a modified output member main body portion instead of the output member main body portion 210. The modified output member main body portion has a function corresponding to the function of the output member main body portion 210 and a structure that differs from that of the output member main body portion 210.

The output functional member 200 in the first embodiment to the fourth embodiment includes the output shaft coupling portion 220. However, the structure of the output functional member 200 is not limited to that exemplified in the embodiments. An output functional member 200 in a modification has the output shaft coupling portion 220 omitted. For example, an output functional member 200 in another modification includes a modified output shaft coupling portion instead of the output shaft coupling portion 220. The modified output shaft coupling portion has a function corresponding to the function of the output shaft coupling portion 220 and a structure that differs from that of the output shaft coupling portion 220.

The output functional member 200 in the first embodiment to the fourth embodiment includes the output side reinforcement portion 231 as the output member reinforcement portion 230. However, the structure of the output functional member 200 is not limited to that exemplified in the embodiments. An output functional member 200 in a modification has the output side reinforcement portion 231 omitted. For example, an output functional member 200 in another modification includes a modified output side reinforcement portion instead of the output side reinforcement portion 231. The modified output side reinforcement portion has a function corresponding to the function of the output side reinforcement portion 231 and a structure that differs from that of the output side reinforcement portion 231. For example, the modified output side reinforcement portion reinforces only one of the output member main body portion 210 and output shaft coupling portion 220. Thus, the output side reinforcement portion 231 may reinforce at least one of the output member main body portion 210 and the output shaft coupling portion 220.

The output functional member 200 in the first embodiment to the fourth embodiment includes the counter side reinforcement portion 232 as the output member reinforcement portion 230. However, the structure of the output functional member 200 is not limited to that exemplified in the embodiments. An output functional member 200 in a modification has the counter side reinforcement portion 232 omitted. For example, an output functional member 200 in another modification includes a modified counter side reinforcement portion instead of the counter side reinforcement portion 232. The modification counter side reinforcement portion has a function corresponding to the function of the counter side reinforcement portion 232 and a structure that differs from that of the counter side reinforcement portion 232.

The output functional member 200 in the first embodiment to the fourth embodiment includes the pushing movement restriction portion 241 as the inner structure protecting portion 240. However, the structure of the output functional member 200 is not limited to that exemplified in the embodiments. An output functional member 200 in a modification has the pushing movement restriction portion 241 omitted. For example, an output functional member 200 in another modification includes a modified pushing movement restriction portion instead of the pushing movement restriction portion 241. The modified pushing movement restriction portion has a function corresponding to the function of the pushing movement restriction portion 241 and a structure that differs from that of the pushing movement restriction portion 241.

The output functional member 200 in the first embodiment to the fourth embodiment includes the pulling movement restriction portion 242 as the inner structure protecting portion 240. However, the structure of the output functional member 200 is not limited to that exemplified in the embodiments. An output functional member 200 in a modification has the pulling movement restriction portion 242 omitted. For example, an output functional member 200 in another modification includes a modified pulling movement restriction portion instead of the pulling movement restriction portion 242. The modified pulling movement restriction portion has a function corresponding to the function of the pulling movement restriction portion 242 and a structure that differs from that of the pulling movement restriction portion 242.

The output functional member 200 in the first embodiment to the fourth embodiment includes the first rotation restriction portion 243 as the inner structure protecting portion 240. However, the structure of the output functional member 200 is not limited to that exemplified in the embodiments. An output functional member 200 in a modification has the first rotation restriction portion 243 omitted. For example, an output functional member 200 in another modification includes a modified first rotation restriction portion instead of the first rotation restriction portion 243. The modified first rotation restriction portion has a function corresponding to the function of the first rotation restriction portion 243 and a structure that differs from that of the first rotation restriction portion 243.

The output functional member 200 in the first embodiment to the fourth embodiment includes the second rotation restriction portion 244 as the inner structure protecting portion 240. However, the structure of the output functional member 200 is not limited to that exemplified in the embodiments. An output functional member 200 in a modification has the second rotation restriction portion 244 omitted. For example, an output functional member 200 in another modification includes a modified second rotation restriction portion instead of the second rotation restriction portion 244. The modified second rotation restriction portion has a function corresponding to the function of the second rotation restriction portion 244 and a structure that differs from that of the second rotation restriction portion 244.

The output functional member 200 in the first embodiment to the fourth embodiment includes the load receiving portion 250. However, the structure of the output functional member 200 is not limited to that exemplified in the embodiments. An output functional member 200 in a modification has the load receiving portion 250 omitted. For example, an output functional member 200 in another modification includes a modified load receiving portion instead of the load receiving portion 250. The modified load receiving portion has a function corresponding to the function of the load receiving portion 250 and a structure that differs from that of the load receiving portion 250.

The output functional member 200 in the first embodiment to the fourth embodiment includes the member receiving portion 260. However, the structure of the output functional member 200 is not limited to that exemplified in the embodiments. An output functional member 200 in a modification has the member receiving portion 260 omitted. For example, an output functional member 200 in another modification includes a modified member receiving portion instead of the member receiving portion 260. The modified member receiving portion has a function corresponding to the function of the member receiving portion 260 and a structure that differs from that of the member receiving portion 260.

A gap is formed between the pushing movement restriction portion 241 in the first embodiment to the fourth embodiment and the main body side pushing restriction portion 33. However, the structure of the pushing movement restriction portion 241 is not limited to that exemplified in the embodiments. No gap is formed between a pushing movement restriction portion 241 in a modification and the main body side pushing restriction portion 33.

A gap is formed between the pulling movement restriction portion 242 in the first embodiment to the fourth embodiment and the main body side pulling restriction portion 34. However, the structure of the pulling movement restriction portion 242 is not limited to that exemplified in the embodiments. No gap is formed between a pulling movement restriction portion 242 in a modification and the main body side pulling restriction portion 34.

The gap is formed between the pulling movement restriction portion 242 in the first embodiment to the fourth embodiment and the main body side rotation restriction portion 35. However, the structure of the pulling movement restriction portion 242 is not limited to that exemplified in the embodiments. No gap is formed between a pulling movement restriction portion 242 in a modification and the main body side rotation restriction portion 35.

The gap is formed between the first rotation restriction portion 243 in the first embodiment to the fourth embodiment and the main body side first restriction portion 35A. However, the structure of the first rotation restriction portion 243 is not limited to that exemplified in the embodiments. No gap is formed between a first rotation restriction portion 243 in a modification and the main body side first restriction portion 35A.

The gap is formed between the second rotation restriction portion 244 in the first embodiment to the fourth embodiment and the main body side second restriction portion 35B. However, the structure of the second rotation restriction portion 244 is not limited to that exemplified in the embodiments. No gap is formed between a second rotation restriction portion 244 in a modification and the main body side second restriction portion 35B.

The size of the gap between the pulling movement restriction portion 242 in the first embodiment to the fourth embodiment and the main body side rotation restriction portion 35 corresponds to the size of the gap between the first rotation restriction portion 243 and the main body side first restriction portion 35A. However, the size of the gap formed by the restriction portions 242 and 35 is not limited to that exemplified in the embodiments. The size of the gap formed between restriction portions 242 and 35 in a modification does not correspond to the size of the gap between the restriction portions 243 and 35A. With the non-corresponding gaps, the rotation amount for the pulling movement restriction portion 242 and the main body side rotation restriction portion 35 to come into contact with each other becomes larger or smaller than the rotation amount for the first rotation restriction portion 243 and the main body side first restriction portion 35A to come into contact with each other.

The size of the gap between the second rotation restriction portion 244 in the first embodiment to the fourth embodiment and the main body side second restriction portion 35B corresponds to the size of the gap between the first rotation restriction portion 243 and the main body side first restriction portion 35A. However, the size of the gap formed by the restriction portions 244 and 35B is not limited to that exemplified in the embodiments. The size of the gap formed between the restriction portions 244 and 35B in a modification does not correspond to the size of the gap between the restriction portions 243 and 35A. With the non-corresponding gaps, the rotation amount for the second rotation restriction portion 244 and the main body side second restriction portion 35B to come into contact with each other becomes larger or smaller than the rotation amount for the first rotation restriction portion 243 and the main body side first restriction portion 35A to come into contact with each other.

The counter functional member 300 in the first embodiment to the fourth embodiment is formed from a metal material. The material of the counter functional member 300 is not limited to that exemplified in the embodiments. For example, a counter functional member 300 in a modification is formed from a resin material.

The counter functional member 300 in the first embodiment to the fourth embodiment is coupled to the counter movable block 70 by the counter movable coupling portion 130. However, how the counter functional member 300 is coupled is not limited to that exemplified in the embodiments. For example, a counter functional member 300 in a modification is directly coupled to the counter movable block 70.

The counter functional member 300 in the first embodiment to the fourth embodiment includes the counter member main body portion 310. However, the structure of the counter functional member 300 is not limited to that exemplified in the embodiments. For example, a counter functional member 300 in a modification includes a modified counter member main body portion instead of the counter member main body portion 310. The modified counter member main body portion has a function corresponding to the function of the counter member main body portion 310 and a structure that differs from that of the counter member main body portion 310.

The counter functional member 300 in the first embodiment to the fourth embodiment includes the counter member adjusting portion 320. However, the structure of the counter functional member 300 is not limited to that exemplified in the embodiments. A counter functional member 300 in a modification has the counter member adjusting portion 320 omitted. For example, a counter functional member 300 in another modification includes a modified counter member adjusting portion instead of the counter member adjusting portion 320. The modified counter member adjusting portion has a function corresponding to the function of the counter member adjusting portion 320 and a structure that differs from that of the counter member adjusting portion 320.

The additional adjustment member 400 in the first embodiment to the third embodiment is formed from a metal material. However, the material of the additional adjustment member 400 is not limited to that exemplified in the embodiments. For example, an additional adjustment member 400 in a modification is formed from a resin material.

The additional adjustment member 400 in the first embodiment to the third embodiment is coupled to the counter member adjusting portion 320 with an adhesive. However, how the additional adjustment member 400 is coupled is not limited to that exemplified in the embodiments. For example, an additional adjustment member 400 in a modification is coupled to the counter member adjusting portion 320 through press fitting or by a fastening member.

The additional adjustment member 400 in the first embodiment to the third embodiment is arranged at a portion on the side of the projecting direction DXL than the counter member adjusting portion 320, in the movable direction DX. However, where the additional adjustment member 400 is arranged is not limited to that exemplified in the embodiments. For example, an additional adjustment member 400 in a modification is arranged at a portion on the side of the retracting direction DXR of the counter member adjusting portion 320, or arranged at portions on the side of the projecting direction DXL and on the side of the retracting direction DXR of the counter member adjusting portion 320.

The electric linear actuator 40 in the first embodiment to the fourth embodiment supplies current to the coil 52 of the fixed block 50 to reciprocate the output movable block 60 and the counter movable block 70. However, the structure for reciprocating the output movable block 60 and the counter movable block 70 is not limited to that exemplified in the embodiments. For example, an electric linear actuator in a modification has any of following structures (a) to (c).

(a) A first modified linear actuator includes a first modified fixed block, a first modified output movable block, and a first modified counter block instead of the fixed block 50, the output movable block 60, and the counter movable block 70.

The first modified fixed block includes a permanent magnet and a back yoke. The first modified fixed block differs from the output movable block 60 and the counter movable block 70 in that the first modified fixed block is fixed to the main body casing 30 but otherwise has the same structure.

The first modified output movable block includes a coil and a core. The first modified output movable block differs from the fixed block 50 in that the first modified output movable block reciprocates in the movable direction DX relative to the main body casing 30 but otherwise has the same structure.

The first modified counter movable block includes a coil and a core. The first modified counter movable block differs from the fixed block 50 in that the first modified counter movable block reciprocates in the movable direction DX relative to the main body casing 30 but otherwise has the same structure.

The first modified linear actuator supplies current to the first modified output movable block and the first modified counter movable block to output the reciprocation. Each movable block reciprocates in the movable direction DX relative to the first modified fixed block due to the electromagnetic force acting between the movable block and the first modified fixed block. The first modified output movable block and the first modified counter movable block reciprocate in the movable direction DX in opposite phases.

(b) The second modified linear actuator includes a second modified output movable block instead of the output movable block 60. In the second modified linear actuator, the fixed block 50 is omitted.

The second modified output movable block includes a coil and a core. The second modified output movable block differs from the fixed block 50 in that the second modified output movable block reciprocates in the movable direction DX relative to the main body casing 30 but otherwise has the same structure.

The second modified linear actuator supplies current to the second modified output movable block to output the reciprocation. The second modified output movable block and the counter movable block 70 reciprocate in the movable direction DX due to the electromagnetic force acting between the movable blocks. The second modified output movable block and the counter movable block 70 reciprocate in the movable direction DX in opposite phases.

(c) The third modified linear actuator includes a third modified counter movable block instead of the counter movable block 70. The third modified linear actuator has the fixed block 50 omitted.

The third modified counter movable block includes a coil and a core. The third modified counter movable block differs from the fixed block 50 in that the third modified counter movable block reciprocates in the movable direction DX relative to the main body casing 30 but otherwise has the same structure.

The third modified linear actuator supplies current to the third modified counter movable block to output the reciprocation. The output movable block 60 and the third modified counter movable block reciprocate in the movable direction DX due to the electromagnetic force acting between the movable blocks. The output movable block 60 and the third modified counter movable block reciprocate in the movable direction DX in opposite phases.

The output shaft vibration-type electric device 10 in the first embodiment to the fourth embodiment includes the elastic member 16 as a single member. However, the structure of the elastic member 16 is not limited to that exemplified in the embodiments. An elastic member in a modification is formed of at least two members. For example, the elastic member according to the modification includes a first elastic member and a second elastic member. The first elastic member has a structure that is substantially the same as a lower portion of an inner side cylindrical portion of the elastic member 16. The second elastic member has a structure that is substantially the same as a portion of the elastic member 16 excluding the lower portion of the inner side cylindrical portion. The inner side cylindrical portion of the elastic member 16 is a cylindrical portion that comes into contact with the output shaft 20.

The output shaft vibration-type electric device 10 in the first embodiment to the fourth embodiment is in the form of an electric toothbrush as an electric oral hygiene device. However, the form of the output shaft vibration-type electric device 10 as the electric oral hygiene device is not limited to that exemplified in the embodiment. For example, a modified output shaft vibration-type electric device may be embodied in an electric interdental brush, an electric dental stain remover, or an electric tongue brush.

The output shaft vibration-type electric device 10 in the first embodiment to the fourth embodiment is in a form an electric oral hygiene device. However, the form of the output shaft vibration-type electric device 10 is not limited to that exemplified in the embodiment. For example, a modified output shaft vibration-type electric device may be embodied in an electric razor or an electric massager.

The invention claimed is:

1. An electric linear actuator configured to drive an output shaft of an output shaft vibration-type electric device, the electric linear actuator comprising:
   a fixed block;
   an output movable block;
   a counter movable block;
   a projecting side coupling member;
   a retracting side coupling member;
   a block coupling member; and
   an output functional member, wherein:
   the electric linear actuator is configured to reciprocate in a projecting direction and a retracting direction that define a movable direction;
   the output movable block and the counter movable block are arranged in parallel in a direction orthogonal to the movable direction;
   the block coupling member is coupled to the fixed block, the output movable block, and the counter movable block;
   the output movable block and the counter movable block are configured to be reciprocated in the movable direction in opposite phases by electromagnetic force acting between the fixed block and the output and counter movable blocks;
   the output functional member is movably coupled to the output movable block, and the output functional member includes a portion arranged further in the projecting direction than the block coupling member;
   the projecting side coupling member is arranged further in the projecting direction than the block coupling member and is coupled to the block coupling member;
   the retracting side coupling member is arranged further in the retracting direction than the block coupling member and is coupled to the block coupling member;
   the projecting side coupling member and the retracting side coupling member have different shapes; and
   the projecting side coupling member is thinner than the retracting side coupling member.

2. An electric linear actuator configured to drive an output shaft of an output shaft vibration-type electric device, the electric linear actuator comprising:
   an output movable block;
   a counter movable block;
   a projecting side coupling member;
   a retracting side coupling member;
   a block coupling member; and
   an output functional member, wherein:
   the electric linear actuator is configured to reciprocate in a projecting direction and a retracting direction that define a movable direction;
   the output movable block and the counter movable block are arranged in parallel in a direction orthogonal to the movable direction;
   the block coupling member is coupled to the output movable block and the counter movable block;
   the output movable block and the counter movable block are configured to be reciprocated in the movable direction in opposite phases by electromagnetic force acting between the output movable block and the counter movable block;
   the output functional member is coupled to the block coupling member, and the output functional member includes a portion arranged further in the projecting direction than the block coupling member;
   the projecting side coupling member is arranged further in the projecting direction than the block coupling member and is coupled to the block coupling member;
   the retracting side coupling member is arranged further in the retracting direction than the block coupling member, and the retracing side coupling member is coupled to the block coupling member;
   the projecting side coupling member and the retracting side coupling member have different shapes; and
   the projecting side coupling member is thinner than the retracting side coupling member.

3. The electric linear actuator according to claim 1, wherein
   the direction orthogonal to the movable direction in a plan view of the electric linear actuator is defined as a width direction, and
   the projecting side coupling member has a shape that is asymmetrical to a center line in the width direction in a side view of the electric linear actuator.

4. The electric linear actuator according to claim 1, further comprising a counter functional member, wherein the counter functional member is coupled to the counter movable block.

5. The electric linear actuator according to claim 1, wherein
   the block coupling member includes an output movable coupling portion, a counter movable coupling portion, a projecting side supporting portion, a retracting side supporting portion, an output side resin inlet portion, a counter side resin inlet portion, an output side resin flow path portion, and a counter side resin flow path portion, wherein the output movable coupling portion, the counter movable coupling portion, the projecting side supporting portion, the retracting side supporting portion, the output side resin inlet portion, the counter side resin inlet portion, the output side resin flow path portion, and the counter side resin flow path portion are formed integrally from a resin material,
the output movable coupling portion is coupled to the output movable block,
the counter movable coupling portion is coupled to the counter movable block,
the projecting side supporting portion is coupled to the output movable coupling portion,
the retracting side supporting portion is coupled to the counter movable coupling portion,
the output side resin flow path portion is continuous with the output movable coupling portion,
the counter side resin flow path portion is continuous with the counter movable coupling portion,
the output side resin inlet portion is continuous with the output side resin flow path portion,
the counter side resin inlet portion is continuous with the counter side resin flow path portion, and
the projecting side coupling member and the retracting side coupling member, which are formed integrally with the block coupling member from the resin material, are continuous with the output movable coupling portion and the counter movable coupling portion.

6. The electric linear actuator according to claim 1, wherein the block coupling member includes a coupling portion supporting surface that receives a load of the output shaft when coupled to a main body casing of the output shaft vibration-type electric device.

7. The electric linear actuator according to claim 2, wherein
the direction orthogonal to the movable direction in a plan view of the electric linear actuator is defined as a width direction, and
the projecting side coupling member has a shape that is asymmetrical to a center line in the width direction in a side view of the electric linear actuator.

8. The electric linear actuator according to claim 2, further comprising a counter functional member, wherein the counter functional member is coupled to the counter movable block.

9. The electric linear actuator according to claim 2, wherein
the block coupling member includes an output movable coupling portion, a counter movable coupling portion, a projecting side supporting portion, a retracting side supporting portion, an output side resin inlet portion, a counter side resin inlet portion, an output side resin flow path portion, and a counter side resin flow path portion, wherein the outpuE movable coupling portion, the counter movable coupling portion, the projecting side supporting portion, the retracting side supporting portion, the output side resin inlet portion, the counter side resin inlet portion, the output side resin flow path portion, and the counter side resin flow path portion are formed integrally from a resin material,
the output movable coupling portion is coupled to the output movable block,
the counter movable coupling portion is coupled to the counter movable block,
the projecting side supporting portion is coupled to the output movable coupling portion,
the retracting side supporting portion is coupled to the counter movable coupling portion,
the output side resin flow path portion is continuous with the output movable coupling portion,
the counter side resin flow path portion is continuous with the counter movable coupling portion,
the output side resin inlet portion is continuous with the output side resin flow path portion,
the counter side resin inlet portion is continuous with the counter side resin flow path portion, and
the projecting side coupling member and the retracting side coupling member, which are formed integrally with the block coupling member from the resin material, are continuous with the output movable coupling portion and the counter movable coupling portion.

10. The electric linear actuator according to claim 2, wherein the block coupling member includes a coupling portion supporting surface that receives a load of the output shaft when coupled to a main body casing of the output shaft vibration-type electric device.

11. An output shaft vibration-type electric device comprising:
an output shaft; and
an electric linear actuator configured to drive the output shaft, wherein the electric linear actuator includes:
a fixed block;
an output movable block;
a counter movable block;
a projecting side coupling member;
a retracting side coupling member;
a block coupling member; and
an output functional member, wherein:
the electric linear actuator is configured to reciprocate in a projecting direction and a retracting direction that define a movable direction;
the output movable block and the counter movable block are arranged in parallel in a direction orthogonal to the movable direction;
the block coupling member is coupled to the fixed block, the output movable block, and the counter movable block;
the output movable block and the counter movable block are configured to be reciprocated in the movable direction in opposite phases by electromagnetic force acting between the fixed block and the output and counter movable blocks;
the output functional member is movably coupled to the output movable block, and the output functional member includes a portion arranged further in the projecting direction than the block coupling member;
the projecting side coupling member is arranged further in the projecting direction than the block coupling member and is coupled to the block coupling member;
the retracting side coupling member is arranged further in the retracting direction than the block coupling member and is coupled to the block coupling member;
the projecting side coupling member and the retracting side coupling member have different shapes;
the projecting side coupling member is thinner than the retracting side coupling member; and
the output shaft is coupled to the output functional member.

12. The output shaft vibration-type electric device according to claim 11, wherein the output shaft vibration-type electric device is embodied in an electric oral hygiene device.

13. An output shaft vibration-type electric device comprising:
- an output shaft; and
- an electric linear actuator configured to drive the output shaft, wherein the electric linear actuator includes:
- an output movable block;
- a counter movable block;
- a projecting side coupling member;
- a retracting side coupling member;
- a block coupling member; and
- an output functional member, wherein:
- the electric linear actuator is configured to reciprocate in a projecting direction and a retracting direction that define a movable direction;
- the output movable block and the counter movable block are arranged in parallel in a direction orthogonal to the movable direction;
- the block coupling member is coupled to the output movable block and the counter movable block;
- the output movable block and the counter movable block are configured to be reciprocated in the movable direction in opposite phases by electromagnetic force acting between the output movable block and the counter movable block;
- the output functional member is coupled to the block coupling member, and the output functional member includes a portion arranged further in the projecting direction than the block coupling member;
- the projecting side coupling member is arranged further in the projecting direction than the block coupling member and is coupled to the block coupling member;
- the retracting side coupling member is arranged further in the retracting direction than the block coupling member, and the retracing side coupling member is coupled to the block coupling member;
- the projecting side coupling member and the retracting side coupling member have different shapes;
- the projecting side coupling member is thinner than the retracting side coupling member; and
- the output shaft is coupled to the output functional member.

14. The output shaft vibration-type electric device according to claim 13, wherein the output shaft vibration-type electric device is embodied in an electric oral hygiene device.

* * * * *